United States Patent
Breslin et al.

(10) Patent No.: US 7,951,797 B2
(45) Date of Patent: May 31, 2011

(54) SUBSTITUTED DIAZEPAN OREXIN RECEPTOR ANTAGONISTS

(75) Inventors: Michael J. Breslin, Drexel Hill, PA (US); Paul J. Coleman, Wallingford, PA (US); Christopher D. Cox, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 721 days.

(21) Appl. No.: 11/998,812

(22) Filed: Nov. 30, 2007

(65) Prior Publication Data

US 2008/0132490 A1 Jun. 5, 2008

Related U.S. Application Data

(60) Provisional application No. 60/872,393, filed on Dec. 1, 2006, provisional application No. 60/959,742, filed on Jul. 16, 2007.

(51) Int. Cl.
*A61P 25/20* (2006.01)
*A61K 31/551* (2006.01)
*C07D 243/08* (2006.01)

(52) U.S. Cl. .................................. 514/218; 540/575
(58) Field of Classification Search ............... 514/218; 540/575
See application file for complete search history.

(56) References Cited

U.S. PATENT DOCUMENTS

| 6,838,465 | B2 | 1/2005 | Yamada et al. | |
|---|---|---|---|---|
| 2006/0258672 | A1 | 11/2006 | Barbosa et al. | |
| 2009/0192143 | A1* | 7/2009 | Cox et al. ............ | 514/221 |
| 2010/0256121 | A1 | 10/2010 | Bergman et al. | |

FOREIGN PATENT DOCUMENTS

| EP | 0794178 | 9/1995 |
|---|---|---|
| WO | WO 00/47576 | 8/2000 |
| WO | WO 01/68609 | 9/2001 |
| WO | WO 01/96302 | 12/2001 |
| WO | WO 02/89800 | 5/2002 |
| WO | WO 02/44172 | 6/2002 |
| WO | WO 02/051838 | 7/2002 |
| WO | WO 02/090355 | 11/2002 |
| WO | WO 03/002559 | 1/2003 |
| WO | WO 03/002561 | 1/2003 |
| WO | WO 03/032991 | 4/2003 |
| WO | WO 03/037847 | 5/2003 |
| WO | WO 03/041711 | 5/2003 |
| WO | WO 03/051368 | 6/2003 |
| WO | WO 03/051873 | 6/2003 |
| WO | WO 2004/004733 | 1/2004 |
| WO | WO 2004/026866 | 4/2004 |
| WO | WO 2004/041816 | 5/2004 |
| WO | WO 2004080976 | 9/2004 |
| WO | WO 2004/085403 | 10/2004 |
| WO | WO 2004/096780 | 11/2004 |
| WO | WO 2005023261 | 3/2005 |
| WO | WO 2005/075458 | 8/2005 |
| WO | WO 2005/118548 | 12/2005 |
| WO | WO 2006/067224 | 6/2006 |
| WO | WO 2006/127550 | 11/2006 |
| WO | WO 2007/025069 | 3/2007 |
| WO | WO 2007/126935 | 11/2007 |
| WO | WO 2008008517 | 1/2008 |
| WO | WO 2008008518 | 1/2008 |
| WO | WO 2008069997 | 6/2008 |
| WO | WO 2009058238 | 5/2009 |

OTHER PUBLICATIONS

Cai, et al., Expert Opn.Ther. Patents, (2006) 16(5), 631-646.
Coleman et al., Bioorg. Med. Chem. Lett., (2010) 20, 2311-2315.
Coleman et al., Expert Opn. Ther. Patents, (2010) 20(3), 307-324.
Coleman et al., "Discovery of MK-4305: A Novel Orexin Receptor Antagonist for the Treatment of Insomnia", Presentation at American Chemical Society 239th National Meeting and Exposition, San Francisco, CA Mar. 12-25, 2010.
Coleman et al., "Discovery of a Novel Orexin Receptor Antagonist for the Treatment of Sleep Disorders", Presentation at 21st Int'l Symposium on Medicinal Chemistry, Brussels, Belgium Sep. 5-9, 2010.
Cox, et al., J. Med. Chem., (2010) 53, 5320-5332.
Cox et al., "Discovery of potent, CNS-penetrant dual orexin receptor antagonists containing a 1,4-diazepan central constraint that promotes sleep in rats", Presentation at the 228th National ACS Meeting, Washington, DC Aug. 20, 2009.
Herring, et al., "MK-4305 Dual Orexin Receptor Antagonist (DORA) Phase IIB Study in Primary Insomnia", Ass'n of Professional Sleep Societies 24th Annual Meeting, San Antonio, Texas Jun. 5-10, 2010.
Sun, et al., "Effects of MK-4305, a Dual Orexin Receptor Antagonist, on Sleep Parameters as Measured by PSG in Healthy Male Subjects", Ass'n of Professional Sleep Societies 24th Annual Meeting, San Antonio, Texas Jun. 5-10, 2010.
Roecker, et al., Current Topics in Med. Chem., (2008), 8, 977-987.
Roecker et al., "Discovery of Potent, Diazepan-containing Dual Orexin Receptor Antagonists for the Treatment of Insomnia", Presentation at the 28th Camerino-Cyprus-Noordwijkerhout Symposium, Camerino Italy, May 19, 2010.
Whitman, et al., ChemMedChem (2009), 4, 1069-1074.
WO 2008/069997, International Preliminary Report on Patentability, Jun. 3, 2009.
EP 07862400, Communication from EPO, Aug. 24, 2009.
EP 07862400, Response submitted to EPO, Mar. 1, 2010.

* cited by examiner

*Primary Examiner* — Brenda L Coleman
(74) *Attorney, Agent, or Firm* — J. Eric Thies; Gerard M. Devlin

(57) ABSTRACT

The present invention is directed to substituted diazepan compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

9 Claims, No Drawings

SUBSTITUTED DIAZEPAN OREXIN RECEPTOR ANTAGONISTS

CROSS REFERENCE TO RELATED APPLICATIONS

This application claims priority under 35 U.S.C. §119(e) from U.S. Ser. No. 60/872,393 filed Dec. 1, 2006 and U.S. Ser. No. 60/959,742 filed Jul. 16, 2007.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric dyskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

Certain orexin receptor antagonists are disclosed in PCT patent publications WO 99/09024, WO 99/58533, WO 00/47576, WO 00/47577, WO 00/47580, WO 01/68609, WO 01/85693, WO 01/96302, WO 2002/044172, WO 2002/051232, WO 2002/051838, WO 2002/089800, WO 2002/090355, WO 2003/002559, WO 2003/002561, WO 2003/032991, WO 2003/037847, WO 2003/041711, WO 2003/051368, WO 2003/051872, WO 2003/051873, WO 2004/004733, WO 2004/026866, WO 2004/033418, WO 2004/041807, WO 2004/041816, WO 2004/052876, WO 2004/083218, WO 2004/085403, WO 2004/096780, WO 2005/060959, WO 2005/075458, WO2005/118548, WO 2006/067224, WO 2006/110626, WO 2006/127550, WO 2007/019234, WO 2007/025069.

SUMMARY OF THE INVENTION

The present invention is directed to diazepan compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

DETAILED DESCRIPTION OF THE INVENTION

The present invention is directed to compounds of the formula I:

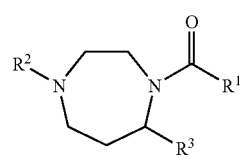

wherein:
$R^1$ is phenyl, which is substituted with $R^{1a}$, $R^{1b}$ and $R^{1c}$;
$R^2$ is heteroaryl, which is substituted with $R^{2a}$, $R^{2b}$ and $R^{2c}$;
$R^{1a}$, $R^{1b}$, $R^{1c}$, $R^{2a}$, $R^{2b}$ and $R^{2c}$ are independently selected from the group consisting of:
  (1) hydrogen,
  (2) halogen,
  (3) hydroxyl,
  (4) —(C=O)$_m$—O$_n$—C$_{1-6}$alkyl, where m is 0 or 1, n is 0 or 1 (wherein if m is 0 or n is 0, a bond is present), wherein adjacent $R^{2a}$ and $R^{2b}$ or $R^{2b}$ and $R^{2c}$ may be joined together to form a cycloalkyl or cycloalkoxy ring, and where the alkyl is unsubstituted or substituted with one or more substituents selected from $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$alkenyl, where the alkenyl is unsubstituted or substituted with one or more substituents selected from $R^{13}$,
(7) —(C=O)$_m$—C$_{2-4}$alkynyl, where the alkynyl is unsubstituted or substituted with one or more substituents selected from $R^{13}$,
(8) —(C=O)$_m$—O$_n$-phenyl or —(C=O)$_m$—O$_n$-napthyl, where the phenyl or napthyl is unsubstituted or substituted with one or more substituents selected from $R^{13}$,
(9) —(C=O)$_m$—O$_n$-heterocycle, where the heterocycle is unsubstituted or substituted with one or more substituents selected from $R^{13}$,
(10) —(C=O)$_m$—NR$^{10}$R$^{11}$, wherein $R^{10}$ and $R^{11}$ are independently selected from the group consisting of:
  (a) hydrogen,
  (b) C$_{1-6}$alkyl, which is unsubstituted or substituted with one or more substituents selected from $R^{13}$,
  (c) C$_{3-6}$alkenyl, which is unsubstituted or substituted with one or more substituents selected from $R^{13}$,
  (d) cycloalkyl, which is unsubstituted or substituted with one or more substituents selected from $R^{13}$,
  (e) phenyl, which is unsubstituted or substituted with one or more substituents selected from $R^{13}$, and
  (f) heterocycle, which is unsubstituted or substituted with one or more substituents selected from $R^{13}$,
(11) —S(O)$_2$—NR$^{10}$R$^{11}$,
(12) —S(O)$_q$—R$^{12}$, where q is 0, 1 or 2 and where $R^{12}$ is selected from the definitions of $R^{10}$ and $R^{11}$,
(13) —CO$_2$H,
(14) —CN,
(15) —NO$_2$,
(16) =O, and
(17) —B(OH)$_2$,
with proviso that at least one of $R^{2a}$, $R^{2b}$ or $R^{2c}$ is halogen or C$_{1-6}$alkyl, or wherein adjacent $R^{2a}$ and $R^{2b}$ or $R^{2b}$ and $R^{2c}$ are joined together to form a cycloalkyl or cycloalkoxy ring, where the alkyl, cycloalkyl or cycloalkoxy is unsubstituted or substituted with one or more substituents selected from $R^{13}$;
$R^3$ is —C$_{1-6}$alkyl or —C$_{3-6}$cycloalkyl, which is unsubstituted or substituted with one or more substituents selected from $R^{13}$;
$R^{13}$ is selected from the group consisting of:
(1) halogen,
(2) hydroxyl,
(3) —(C=O)$_m$—O$_n$—C$_{1-6}$alkyl, where the alkyl is unsubstituted or substituted with one or more substituents selected from $R^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from $R^{14}$,
(6) —(C=O)$_m$—C$_{2-4}$alkenyl, where the alkenyl is unsubstituted or substituted with one or more substituents selected from $R^{14}$,
(7) —(C=O)$_m$—O$_n$-phenyl or —(C=O)$_m$—O$_n$-napthyl, where the phenyl or napthyl is unsubstituted or substituted with one or more substituents selected from $R^{14}$,
(8) —(C=O)$_m$—O$_n$-heterocycle, where the heterocycle is unsubstituted or substituted with one or more substituents selected from $R^{14}$,
(9) —(C=O)$_m$—NR$^{10}$R$^{11}$,
(10) —S(O)$_2$—NR$^{10}$R$^{11}$,
(11) —S(O)$_q$—R$^{12}$,
(12) —CO$_2$H,
(13) —CN,
(14) =O, and
(15) —NO$_2$;
$R^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heterocycle,
(10) —CO$_2$H, and
(11) —CN;
or a pharmaceutically acceptable salt thereof.

An embodiment of the present invention includes compounds of the formula Ia:

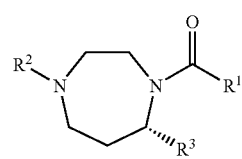

Ia wherein $R^1$, $R^2$ and $R^3$ are defined herein; or a pharmaceutically acceptable salt thereof.

An embodiment of the present invention includes compounds of the formula Ib:

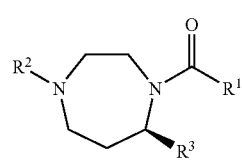

Ib wherein $R^1$, $R^2$ and $R^3$ are defined herein; or a pharmaceutically acceptable salt thereof.

An embodiment of the present invention includes compounds of the formula Ic:

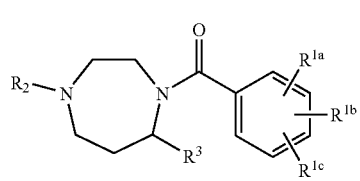

Ic wherein $R^{1a}$, $R^{1b}$, $R^{1c}$, $R^2$ and $R^3$ are defined herein; or a pharmaceutically acceptable salt thereof.

An embodiment of the present invention includes compounds of the formula Id:

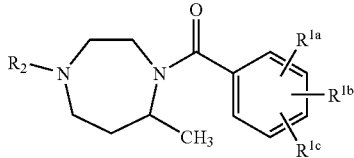

wherein $R^{1a}$, $R^{1b}$, $R^{1c}$ and $R^2$ are defined herein; or a pharmaceutically acceptable salt thereof.

An embodiment of the present invention includes compounds of the formula Ie:

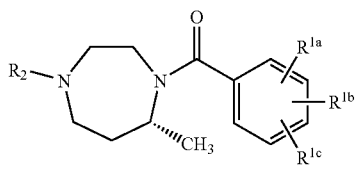

wherein $R^{1a}$, $R^{1b}$, $R^{1c}$ and $R^2$ are defined herein; or a pharmaceutically acceptable salt thereof.

An embodiment of the present invention includes compounds wherein
$R^1$ is phenyl, which is unsubstituted or substituted with one or more of:
(1) halogen,
(2) hydroxyl,
(3) —$O_n$—$C_{1-6}$alkyl, where n is 0 or 1 (wherein if n is 0, a bond is present) and where the alkyl is unsubstituted or substituted with one or more substituents selected from $R^{13}$,
(4) —$O_n$-phenyl, where the phenyl is unsubstituted or substituted with one or more substituents selected from $R^{13}$,
(5) -heterocycle, where the heterocycle is unsubstituted or substituted with one or more substituents selected from $R^{13}$,
(6) —$NR^{10}R^{11}$, wherein $R^{10}$ and $R^{11}$ are independently selected from the group consisting of:
  (a) hydrogen,
  (b) $C_{1-6}$alkyl, which is unsubstituted or substituted with one or more substituents selected from $R^{13}$,
(7) —$S(O)_2$—$NR^{10}R^{11}$,
(8) —$CO_2H$,
(9) —CN,
(10) —$NO_2$, and
(11) —$B(OH)_2$.

An embodiment of the present invention includes compounds wherein
$R^1$ is phenyl, which is unsubstituted or substituted with one or more methyl, —$CF_3$, halo, —$OCF_3$, —$OCH_3$, —$OCH_2CH_3$, —$CO_2CH_3$, —CN, —$N(CH_3)$, —$NH(CH_2CH_3)$, —$NO_2$, —$B(OH)_2$, triazolyl or phenyl:

An embodiment of the present invention includes compounds wherein
$R^1$ is phenyl, which is unsubstituted or substituted with one or more methyl, —$CF_3$, chloro, fluoro, —$OCF_3$, —$OCH_3$, —$OCH_2CH_3$, —$CO_2CH_3$, —$B(OH)_2$, triazolyl or phenyl.

An embodiment of the present invention includes compounds wherein
$R^1$ is phenyl, which is unsubstituted or substituted with one or more methyl, —$CF_3$, fluoro, —$OCF_3$, —$OCH_3$, —$CO_2CH_3$, —$B(OH)_2$, triazolyl or phenyl.

An embodiment of the present invention includes compounds wherein
$R^1$ is selected from the group consisting of:
(1) phenyl,
(2) biphenyl,
(3) 2,6-dimethoxyphenyl,
(4) 2,4-dichlorophenyl,
(5) 2,6-dichlorophenyl,
(6) 2,3-difluophenyl,
(7) 2,4-difluophenyl,
(8) 2,6-difluophenyl,
(9) 2-methoxy-4-methyl-phenyl,
(10) 3-methoxy-biphenyl,
(11) 3-methyl-biphenyl, and
(12) 5-methyl-2-triazolyl-phenyl.

An embodiment of the present invention includes compounds wherein
$R^1$ is phenyl, which is unsubstituted or substituted with one or more methyl or triazolyl. An embodiment of the present invention includes compounds wherein $R^1$ is phenyl. An embodiment of the present invention includes compounds wherein $R^1$ is triazolyl phenyl or triazolyl(methyl)phenyl. An embodiment of the present invention includes compounds wherein
$R^1$ is 5-methyl-2-triazolyl-phenyl.

An embodiment of the present invention includes compounds wherein
$R^2$ is heteroaryl, which is unsubstituted or substituted with one or more of:
(1) halogen,
(2) hydroxyl,
(3) —$O_n$—$C_{1-6}$alkyl, where n is 0 or 1 (wherein if n is 0, a bond is present) and where the alkyl is unsubstituted or substituted with one or more substituents selected from $R^{13}$,
(4) —$O_n$-phenyl, where the phenyl is unsubstituted or substituted with one or more substituents selected from $R^{13}$,
(5) -heterocycle, where the heterocycle is unsubstituted or substituted with one or more substituents selected from $R^{13}$,
(6) —$NR^{10}R^{11}$, wherein $R^{10}$ and $R^{11}$ are independently selected from the group consisting of:
  (a) hydrogen,
  (b) $C_{1-6}$alkyl, which is unsubstituted or substituted with one or more substituents selected from $R^{13}$,
(7) —$S(O)_2$—$NR^{10}R^{11}$,
(8) —$CO_2H$,
(9) —CN, and
(10) —$NO_2$,
with proviso that at least one of the substituents is halogen or $C_{1-6}$alkyl, or wherein two adjacent substituents are joined together to form a cycloalkyl ring.

An embodiment of the present invention includes compounds wherein
$R^2$ is heteroaryl, which is substituted with halogen or $C_{1-6}$alkyl, and optionally substituted with hydroxyl, —O—$C_{1-6}$alkyl or phenyl.

An embodiment of the present invention includes compounds wherein one of $R^{2a}$, $R^{2b}$ and $R^{2c}$ is halogen or $C_{1-6}$alkyl, and the others of $R^{2a}$, $R^{2b}$ and $R^{2c}$ are hydrogen. Within this embodiment the present invention includes compounds wherein one of $R^{2a}$, $R^{2b}$ and $R^{2c}$ is chloro, fluoro or methyl, and the others of $R^{2a}$, $R^{2b}$ and $R^{2c}$ are hydrogen. An embodiment of the present invention includes compounds wherein two of $R^{2a}$, $R^{2b}$ and $R^{2c}$ are joined together to for a $C_{1-6}$alkyl ring, and the other of $R^{2a}$, $R^{2b}$ and $R^{2c}$ is hydrogen. Within this embodiment the present invention includes compounds wherein two of $R^{2a}$, $R^{2b}$ and $R^{2c}$ are joined together to for a $C_{1-6}$alkyl ring which is substituted with =O, and the other of $R^{2a}$, $R^{2b}$ and $R^{2c}$ is hydrogen.

An embodiment of the present invention includes compounds wherein
$R^2$ is selected from the group consisting of:
(1) benzimidazolyl,
(2) benzothiazolyl,
(3) benzoxazolyl,
(4) cyclopentylpyrimidinyl,
(5) dihydrocyclopentapyrimidinyl,
(6) dihydroquinolinyl,
(7) furopyrimidinyl,
(8) pyrazolopyrimidinyl,
(9) pyridinyl,
(10) pyridopyrimidinyl,
(11) pyrimidinyl,
(12) quinazolinyl,
(13) quinolinyl,
(14) quinoxalinyl,
(15) tetrahydroquinazolinyl,
(16) thiadiazolyl, and
(17) thienopyrimidinyl,
which is substituted with halogen or $C_{1-6}$alkyl, and optionally substituted with hydroxyl, —O—$C_{1-6}$alkyl, keto, —NH$_2$, or phenyl.

An embodiment of the present invention includes compounds wherein
$R^2$ is selected from the group consisting of:
(1) 1,3-benzoxazol-2-yl,
(2) 2-(6,7-dihydro-5H-cyclopenta[d]pyrimidin)-yl,
(3) 2-(7,8-dihydroquinolin-5(6H)-on)-yl,
(4) 2-(furo[2,3]pyrimidine)-yl,
(5) 2-(pyrazolo[3,4]pyrimidine)-yl,
(6) 2-pyridinyl,
(7) 2-(pyrido[2,3-d]pyrimidin-7(8H)-on)-yl,
(8) 2-pyrimidinyl,
(9) 2-quinazolinyl,
(10) 2-quinoxalinyl,
(11) 2-(5,6,7,8-tetrahydroquinazolin)-yl,
(12) 2-(thieno[2,3-d]pyrimidin)-yl, and
(13) 2-(thieno[2,3]pyrimidin-4-amine)-yl,
which is substituted with methyl, chloro or fluoro.

An embodiment of the present invention includes compounds wherein
$R^2$ is selected from the group consisting of:
(1) 1,3-benzoxazol-2-yl,
(2) 2-pyrimidinyl,
(3) 2-quinazolinyl,
(4) 2-quinoxalinyl, and
(5) 2-(thieno[2,3]pyrimidin-4-amine)-yl,
which is substituted with methyl, chloro or fluoro.

An embodiment of the present invention includes compounds wherein
$R^2$ is benzoxazoly which is substituted with methyl, chloro or fluoro.

An embodiment of the present invention includes compounds wherein
$R^2$ is pyrimidinyl which is substituted with methyl, chloro or fluoro.

An embodiment of the present invention includes compounds wherein
$R^2$ is quinazolinyl which is substituted with methyl, chloro or fluoro.

An embodiment of the present invention includes compounds wherein
$R^2$ is quinoxalinyl which is substituted with methyl, chloro or fluoro.

An embodiment of the present invention includes compounds wherein
$R^2$ is (thieno[2,3]pyrimidin-4-amine)-yl which is substituted with methyl, chloro or fluoro.

An embodiment of the present invention includes compounds wherein
$R^2$ is other than 6-chloro-benzothiazolyl.

An embodiment of the present invention includes compounds wherein $R^3$ is —$C_{1-6}$alkyl which is unsubstituted or substituted with one or more substituents selected from $R^{13}$.

An embodiment of the present invention includes compounds wherein $R^3$ is —$C_{1-6}$alkyl, which is unsubstituted or substituted with one or more substituents selected from the group consisting of:
(1) halogen,
(2) hydroxyl,
(3) —$C_{1-6}$alkyl,
(4) —($C_{1-3}$)perfluoroalkyl,
(5) —O—($C_{1-3}$)perfluoroalkyl,
(6) —$C_{3-6}$cycloalkyl, and
(7) —$C_{2-4}$alkenyl.

An embodiment of the present invention includes compounds wherein $R^3$ is —$C_{1-6}$alkyl. Within this embodiment the present invention includes compounds wherein $R^3$ is selected from the group consisting of: methyl, ethyl, n-propyl, iso-propyl, n-butyl, iso-butyl, tert-butyl, n-pentyl, iso-pentyl, neo-pentyl and hexyl. Within this embodiment the present invention includes compounds wherein $R^3$ is methyl.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual enantiomers or diastereomers thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 ug/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 11 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 ul assay buffer and then incubated for 60 min (37° C., 5% CO2) in 60 ul assay buffer containing 1 uM Fluo-4AM ester, 0.02% pluronic acid, and 1% BSA. The dye loading solution is then aspirated and cells are washed 3 times with 100 ul assay buffer. 30 ul of that same buffer is left in each well. Within the Fluorescent Imaging Plate Reader (FLIPR, Molecular Devices), test compounds are added to the plate in a volume of 25 ul, incubated for 5 min and finally 25 ul of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. The intrinsic orexin receptor antagonist activity of a compound which may be used in the present invention may be determined by these assays.

In particular, the compounds of the following examples had activity in antagonizing the rat orexin-1 receptor and/or the human orexin-2 receptor in the aforementioned assays, generally with an $IC_{50}$ of less than about 50 μM. Many of compounds within the present invention had activity in antagonizing the rat orexin-1 receptor and/or the human orexin-2 receptor in the aforementioned assays with an $IC_{50}$ of less than about 100 nM. Such a result is indicative of the intrinsic activity of the compounds in use as antagonists of orexin-1 receptor and/or the orexin-2 receptor. The present invention also includes compounds within the generic scope of the invention which possess activity as agonists of the orexin-1 receptor and/or the orexin-2 receptor. With respect to other diazepan compounds, the present compounds exhibit unexpected properties, such as with respect to increased oral bioavailability, metabolic stability, time-dependent inhibition, and/or selectivity with respect to other receptors.

The orexin receptors have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof which comprises administering to the patient a therapeutically effective amount of a compound of the present invention.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in continuation with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD); GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate, miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activator receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo; (g) PPARδ agonists; (h) PPAR α/δ agonists, such as muraglitazar, and the compounds disclosed in U.S. Pat. No. 6,414,002; and (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065; (18) galanin antagonists; (19) CCK agonists; (20) CCK-A (cholecystokinin-A) agonists, such as AR-R 15849, GI 181771, JMV-180, A-71378, A-71623 and SR14613; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6,beta-Ala11,Phe13,Nle14]Bn(6-14) and [D-Phe6,Phe13]Bn(6-13) propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5, 5,8,8-tetramethyl-2-napthalenyl)-1-propenyl]benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, MK-431, P93/01, TSL 225, TMC-2A/2B/2C, FE 999011, P9310/K364, VIP 0177, SDZ 274-444; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, G1-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitor such as BVT 3498, BVT 2733; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; DEAD: diethylazodicarboxylate; DIPEA: N,N-diisopropylethylamine; DMSO: dimethylsulfoxide; EDC: N-(3-Dimethylaminopropyl)-N'-ethylcarbodiimide; HOBT: hydroxybenzotriazole hydrate; Boc: tert-butyloxy carbonyl; $Et_3N$: triethylamine; DCM: dichloromethane; DCE: dichloroethane; BSA: bovine serum albumin; TFA: trifluoracetic acid; DMF: N,N-dimethylformamide; MTBE: methyl tert-butyl ether; $SOCl_2$: thionyl chloride; CDI: carbonyl diimidazole; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

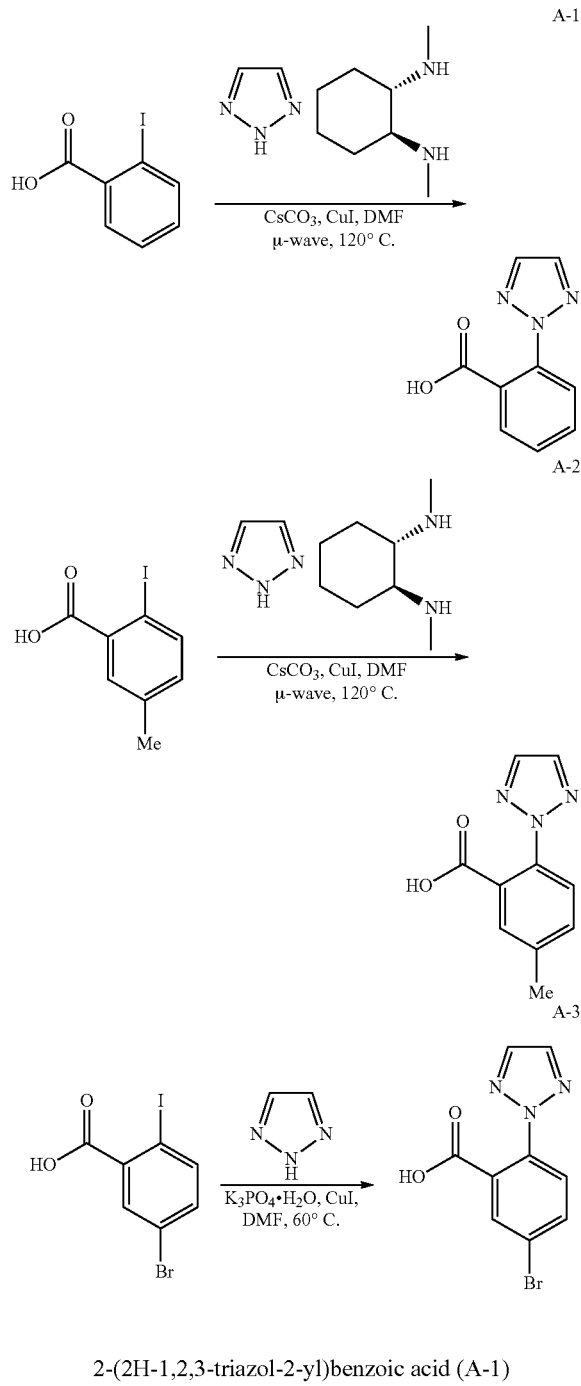

SCHEME A 2-(2H-1,2,3-triazol-2-yl)benzoic acid (A-1)

A solution of 2-iodobenzoic acid (3.0 g, 12.09 mmol) in DMF was treated with (1.5 g, 21.7 mmol) 1,2,3-triazole, 7.08 g (21.7 mmol) C$_s$CO$_3$, 114 mg (0.60 mmol) CuI and 310 mg (2.17 mmol) trans-N,N'-dimethylcyclohexane-1,2-diamine. The mixture was heated at 120° C. for 10 min in a microwave reactor. The reaction was cooled to rt, diluted with EtOAc, and filtered through Celite. The residue was purified by gradient elution on SiO$_2$ (MeOH in DCM with 0.1% AcOH) to give the faster eluting desired 2-(2H-1,2,3-triazol-2-yl)benzoyl acid, A-1. Data for A-1: $^1$HNMR (500 MHz, DMSO-d$_6$) δ 13.05 (br s, 1H), 8.12 (s, 2H), 7.81-7.52 (m, 4H) ppm. The undesired 2-(1H-1,2,3-triazol-2-yl)benzoic acid eluted second.

2-(2H-1,2,3-triazol-2-yl)-5-methylbenzoic acid (A-2)

A solution of 2-iodo-5-methylbenzoic acid (4.0 g, 15.3 mmol) in DMF (10 mL) was treated with 1,2,3-triazole (2.1 g, 30.5 mmol), CsCO$_3$ (9.95 g, 30.5 mmol), CuI (0.145 g, 0.76 mmol) and trans-N,N'-dimethylcyclohexane-1,2-diamine (0.43 g, 3.05 mmol). The mixture was heated at 120° C. for 10 min in a microwave reactor. The reaction was cooled to room temperature, diluted with water, and washed with EtOAc. The aqueous phase was acidified with 1N HCl and extracted with EtOAc. The organic layer was dried over Na$_2$SO$_4$, filtered and concentrated. The residue was purified by gradient elution on SiO$_2$ (MeOH in DCM with 0.1% AcOH) to give the faster eluting 2-(2H-1,2,3-triazol-2-yl)-5-methylbenzoic acid A-2, followed by the undesired regioisomer isomer, 2-(1H-1,2,3-triazol-2-yl)-5-methylbenzoic acid. Data for A-2: $^1$HNMR (500 MHz, DMSO-d$_6$) δ 12.98 (br s, 1H), 8.04 (s, 2H), 7.72-7.45 (m, 3H), 2.41 (s, 3H) ppm.

5-bromo-2-(2H-1,2,3-triazol-2-yl)benzoic acid (A-3)

A solution of 5-bromo-2-iodobenzoic acid (10.0 g, 30.6 mmol) in DMF was treated with (2.11 g, 30.6 mmol) 1,2,3-triazole, 14.09 g (61.2 mmol) K$_3$PO$_4$.H$_2$O and 583 mg (3.06 mmol) CuI. The mixture was heated at 60° C. for 3 hours with stirring under N$_2$. The reaction was cooled to rt, diluted with water and acidified with 1N HCl. The mixture was partitioned with EtOAc three times. The organic layers were combined, rinsed with brine, dried over MgSO$_4$, filtered and concentrated. The residue was purified by column chromatography (EtOAc in hexanes, 1% AcOH buffer) to give the faster eluting desired 5-bromo-2-(2H-1,2,3-triazol-2-yl)benzoic acid, A-3. Data for A-3: $^1$HNMR (500 MHz, DMSO-d$_6$) δ 13.4 (br s, 1H), 8.12 (m, 2H), 7.94-7.88 (m, 2H), 7.78-7.73 (m, 1H) ppm. The undesired 5-bromo-2-(1H-1,2,3-triazol-2-yl)benzoic acid eluted second.

SCHEME B

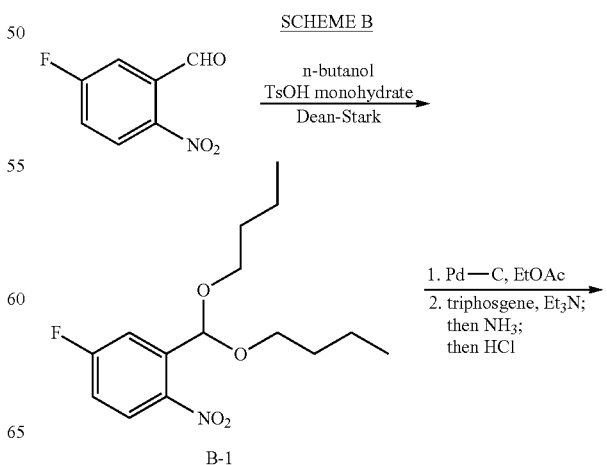

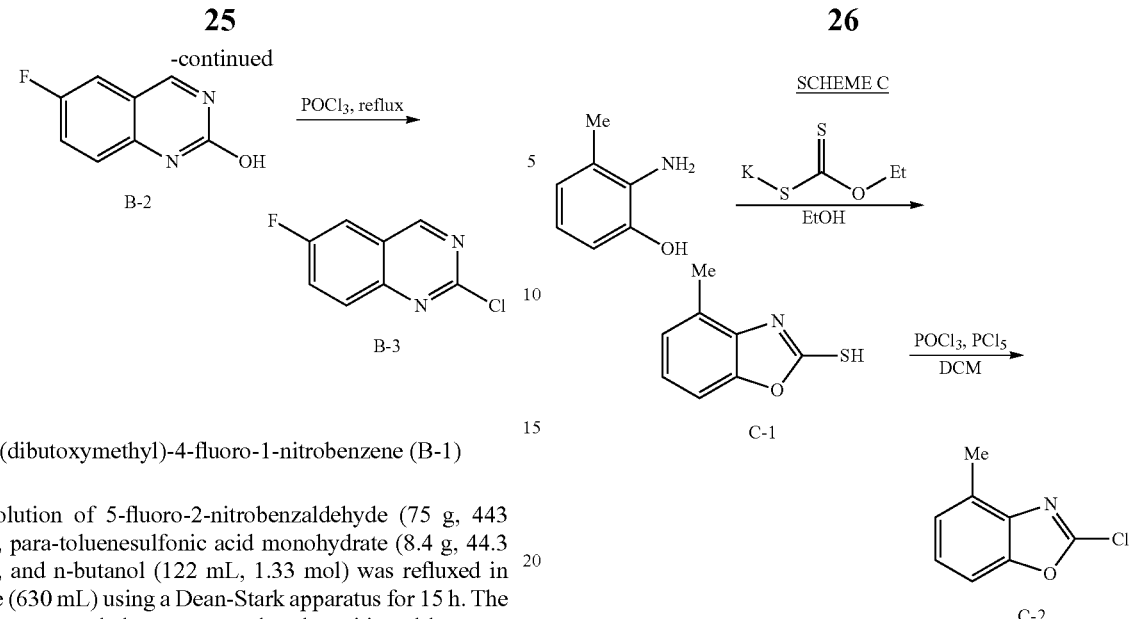

2-(dibutoxymethyl)-4-fluoro-1-nitrobenzene (B-1)

A solution of 5-fluoro-2-nitrobenzaldehyde (75 g, 443 mmol), para-toluenesulfonic acid monohydrate (8.4 g, 44.3 mmol), and n-butanol (122 mL, 1.33 mol) was refluxed in toluene (630 mL) using a Dean-Stark apparatus for 15 h. The reaction was cooled, concentrated and partitioned between water (1 L) and EtOAc (1 L). The organic layer was washed with water (1 L) and brine (1 L), dried over $Na_2SO_4$ and concentrated. The crude reaction was purified by column chromatography (EtOAc in hexanes, 1% triethylamine buffer) to yield B-1 as an oil. Data for B-1: $^1$HNMR (500 MHz, $CDCl_3$) δ 7.92 (dd, J=8.5, 4.5 Hz, 1H), 7.54 (dd, J=9.0, 3.0 Hz, 1H), 7.15-7.11 (m, 1H), 6.05 (s, 1H), 3.67-3.52 (m, 4H), 1.63-1.57 (m, 4H), 1.43-1.35 (m, 4H), 0.94-0.91 (m, 6H) ppm; LRMS (M+H) m/z=169.8 found; 300.3 required (see loss of acetal).

2-chloro-6-fluoroquinazoline (B-3)

To a solution of B-1 (26.1 g, 87 mmol) in EtOAc (350 mL) under nitrogen atmosphere at 25° C. was added Pd—C (10 wt %, 2.3 g) and the reaction was placed under hydrogen atmosphere (1 atm). The reaction was stirred 12 h, filtered through celite and concentrated. The residue was redissolved in THF (350 mL) and cooled to 0° C. To this solution was added triethylamine (45.0 mL, 323 mmol) and triphosgene (8.6 g, 29.1 mmol) in THF (60 mL) dropwise. The reaction was stirred 10 minutes and ammonia in methanol (46.1 mL, 323 mmol, 7M solution) was added. The reaction was stirred at 0° C. for 10 minutes and quickly warmed to ambient temperature. After 15 minutes at room temperature, the reaction was acidified with 4M HCl in dioxane (120 mL) to pH 2. The reaction was stirred at room temperature for 1 hour and concentrated directly. The residue was azeotroped with toluene and methanol to give B-2 as a yellow cake. Data for B-2: LRMS m/z (M+H)=164.9 found; 165.1 required. The yellow cake was dissolved in neat phosphorous oxychloride (130 mL) and refluxed (120° C.) for 1 hour. The reaction was cooled and the excess solvent was removed in vacuo. The crude reaction mixture was dissolved in EtOAc (600 mL) and quenched slowly at 0° C. with water (500 mL). The aqueous phase was extracted with EtOAc (2×200 mL) and the combined organic phase was dried over $MgSO_4$ and concentrated. The crude reaction was purified by column chromatography (EtOAc/dichloromethane) to afford B-3 as an off-white solid. Data for B-3: $^1$HNMR (500 MHz, $CDCl_3$) δ 9.29 (s, 1H), 8.04 (dd, J=9.0, 5.0 Hz, 1H), 7.77-7.72 (m, 1H), 7.59 (dd, J=7.5, 2.5 Hz, 1H) ppm; LRMS m/z (M+H)=183.2 found; 183.0 required.

SCHEME C

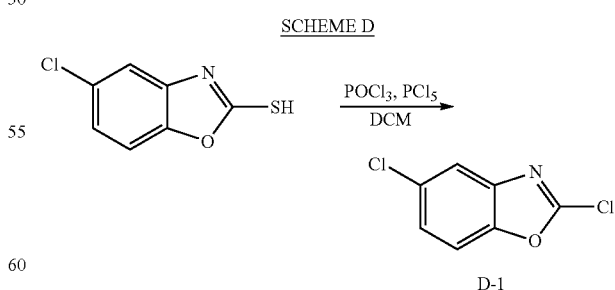

4-methyl-1,3-benzoxazole-2-thiol (C-1)

A solution of 2-amino-m-cresol (4.0 g, 32.5 mmol) and potassium ethylxanthate (10.4 g, 65.0 mmol) in 30 mL of EtOH was refluxed for 3 h. The solvent was removed by rotary evaporation, the residue was dissolved in approximately 50 mL of water and acetic acid was added to adjust the pH to ~5. The solid thus formed was collected by filtration and dried under vacuum to provide C-1 as a white solid. Data for C-1: LC/MS: rt=1.67 min; m/z (M+H)=166.0 found; 166.0 required.

2-chloro-4-methyl-1,3-benzoxazole (C-2)

To a suspension of C-1 (1.6 g, 9.7 mmol) in $POCl_3$ (4.5 mL, 48.4 mmol) was added $PCl_5$ (2.2 g, 10.6 mmol) and about 10 mL $CH_2Cl_2$. After stirring overnight, the solvents were removed by rotary evaporation, the residue was partitioned between $CH_2Cl_2$ and 5% aqueous $Na_2CO_3$. The layers were separated, the organic was washed with water, dried over $Na_2SO_4$, and concentrated. The residue was purified by silica gel chromatography (EtOAc/hexanes) to provide C-2 as a white solid. Data for C-2: LC/MS: rt=2.28 min; m/z (M+H)= 168.0 found; 168.0 required.

SCHEME D 2,5-dichloro-1,3-benzoxazole (D-1)

To a suspension of 5-chloro-2-mercaptobezoxazole (5.0 g, 26.9 mmol) in $POCl_3$ (12.6 mL, 135 mmol) was added $PCl_5$ (6.2 g, 129.6 mmol) and about 20 mL CH$_2$Cl$_2$. After stirring 5 days, the solvents were removed by rotary evaporation, the residue was partitioned between EtOAc and saturated aqueous NaHCO$_3$. The layers were separated, the organic was washed with brine, dried over Na$_2$SO$_4$, and concentrated. The residue was dissolved in a minimum amount of CHCl$_3$, hexanes were added, and a small amount of solids were filtered off. The filtrate was concentrated to provide D-1 as a white solid. Data for D-1: LC/MS: rt=2.38 min; m/z (M+H)=188.0 found; 188.0 required.

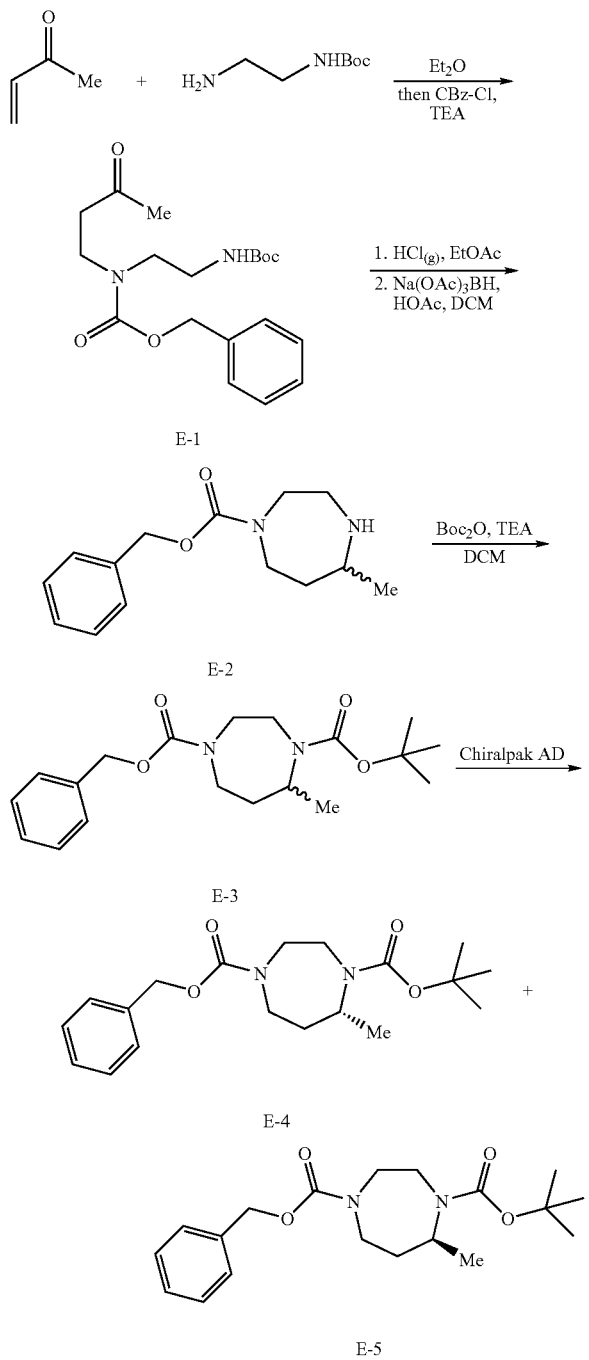

methyl ketone (E-1)

A solution of Boc-ethylenediamine (20.0 g, 125 mmol) in 250 mL Et$_2$O was treated dropwise with 10.2 mL (125 mmol) methyl vinyl ketone and was allowed to stir 24 h. The reaction was then cooled to 0° C. and 22.6 mL (162 mmol) triethylamine was added, followed by 19.6 mL (137 mmol) benzyl chloroformate. The reaction was allowed to slowly warm to room temperature with stirring overnight. The reaction was diluted with EtOAc, washed with an aqueous 10% citric acid solution, then with saturated NaHCO$_3$, and then brine. The organic phase was dried over Na$_2$SO$_4$, filtered and concentrated to provide E-1 as a pale yellow oil. Data for E-1: LC/MS: rt=2.22 min, m/z (M+H)=265.2 found; 365.2 required (see loss of Boc group).

benzyl 5-methyl-1,4-diazepane-1-carboxylate (E-2)

A solution of 39.0 g (107 mmol) E-1 in 300 mL EtOAc was saturated with HCl(g), the flask was capped and allowed to stir 2 h. The solvents were removed by rotary evaporation, the residue was dissolved in 1M HCl, washed with Et$_2$O, basified with NaOH, and extracted three times with 2:1 CHCl$_3$/EtOH. The combined organic phases were washed with brine, concentrated, dissolved in CH$_2$Cl$_2$ and filtered to provide 19.2 g of a brown oil. This material was dissolved in 200 mL CH$_2$Cl$_2$ and to this was added 5 mL of HOAc. After stirring for 2 h, 23.1 g (109 mmol) of Na(OAc)$_3$BH was added and the resultant mixture was stirred 48 h at room temperature. Some of the solvent was removed by rotary evaporation, and the residue was dumped into a separatory funnel containing a saturated NaHCO$_3$ solution and 2:1 CHCl$_3$/EtOH. The layers were separated, and the aqueous was extracted twice more with 2:1 CHCl$_3$/EtOH. The combined organic layers were washed with a minimum amount of brine, concentrated, dissolved in CH$_2$Cl$_2$, filtered and concentrated to provide E-2 as a brown oil. Data for E-2: LC/MS: rt=1.12 min; m/z (M+H)=249.1 found; 249.2 required.

1-benzyl 4-tert-butyl 5-methyl-1,4-diazepane-1,4-dicarboxylate (E-3)

To a solution of 23.8 g (96 mmol) of E-2 in 200 mL CH$_2$Cl$_2$ was added 26.7 mL (192 mmol) triethylamine and 25.1 g (115 mmol) di-tert-butyl dicarbonate. After stirring overnight at room temperature, the reaction was diluted with CH$_2$Cl$_2$ and dumped into a separatory funnel, washed with a saturated NaHCO$_3$ solution, dried over Na$_2$SO$_4$, and concentrated. The residue was purified by silica gel chromatography (EtOAc/hexanes) to provide E-3 as a colorless oil. Data for E-3: LC/MS: rt=2.64 min; m/z (M+H)=249.2 found; 349.4 required (see loss of Boc group).

1-benzyl 4-tert-butyl (5R)-5-methyl-1,4-diazepane-1,4-dicarboxylate (E-4) and 1-benzyl 4-tert-butyl (5S)-5-methyl-1,4-diazepane-1,4-dicarboxylate (E-5)

The enantiomers of E-3 were separated preparatively on a 10 cm×50 cm Chiralpak AD column by isocratic elution with 60% EtOH and 40% hexanes (containing 0.1% diethylamine) at a flow rate of 175 mL/minute. Approximately 6 g of E-3 could be separated in one run under these conditions. Analytical analysis was performed on a 0.46 cm×25 cm Chrialpak AD column with 60% EtOH and 40% hexanes (containing 0.1% diethylamine) at a flow rate of 1 mL/minute. The first enantiomer to elute (E-4), believed to be the (R)-enantiomer, is the desired isomer and had a retention time of 4.12 minutes.

It was a colorless gum of >98% ee. The second enantiomer to elute (E-5), believed to be the (S)-enantiomer, is the undesired isomer and had a retention time of 4.82 minutes. It was a colorless gum of ~90 ee.

SCHEME F

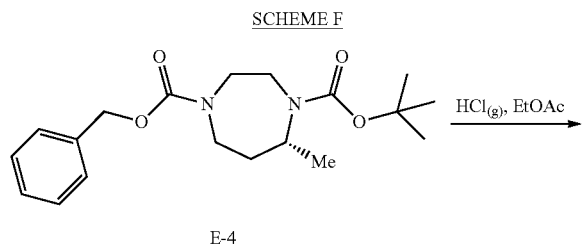

E-4

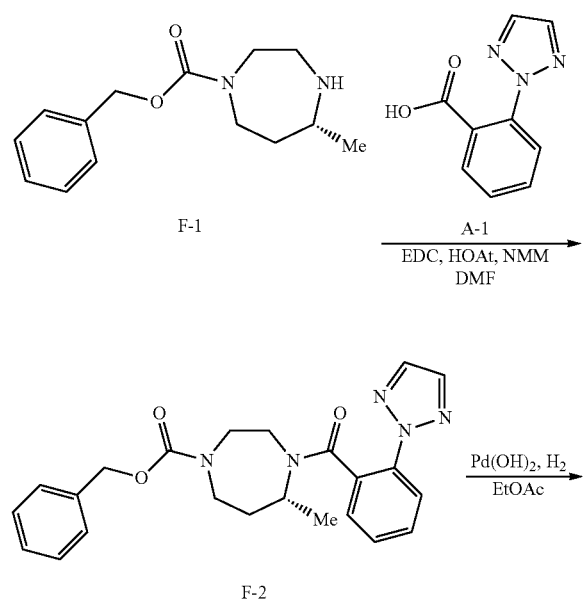

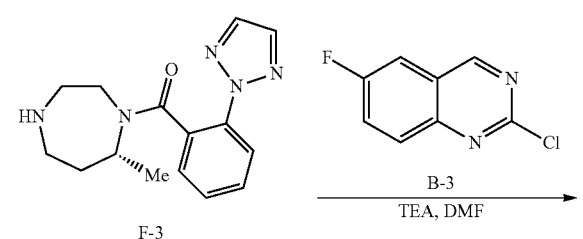

F-4 benzyl (5R)-5-methyl-1,4-diazepane-1-carboxylate (F-1)

A solution of 15.0 g (43.0 mmol) E-4 in 350 mL EtOAc was saturated with HCl(g), the flask was capped and allowed to stir 15 minutes. The solution was again saturated with HCl(g), the flask was capped and allowed to stir 30 minutes before the volatiles were removed by rotary evaporation to provide 13.0 g of the hydrochloride salt of F-1 as a colorless gum. Data for F-1: LC/MS: rt=1.10 min; m/z (M+H)=249.2 found; 249.3 required.

benzyl (5R)-5-methyl-4-[2-(2H-1,2,3-triazol-2-yl) benzoyl]-1,4-diazepane-1-carboxylate (F-2)

To a solution of 12.0 g (42.3 mmol) of the hydrochloride salt of F-1, 8.8 g (46.6 mmol) A-1, 6.92 g (50.8 mmol) 1-hydroxy-7-azabenzotriazole, and 18.6 mL (169 mmol) N-methylmorpholine in 200 mL of DMF was added 12.2 g (63.5 mmol) EDC and the reaction was stirred overnight at room temperature. The reaction was partitioned between EtOAc and 10% aqueous $KHSO_4$, washed with water, saturated aqueous $NaHCO_3$, water, brine, dried over $MgSO_4$, and concentrated by rotary evaporation. The previous acidic and basic layers were extracted again with EtOAc. The organic extract was washed with brine, dried, concentrated and combined with the organic residue from above. The total amount of residue was purified by column chromatography on silica gel (EtOAc/hexanes) to provide F-2 as a colorless oil. Data for F-2: LC/MS: rt=2.25 min; m/z (M+H)=420.3 found; 420.5 required.

(7R)-7-methyl-1-[2-(2H-1,2,3-triazol-2-yl)benzoyl]-1,4-diazepane (F-3)

A round bottom flask containing a solution of 12.2 g (29.0 mmol) F-2 in 250 mL EtOAc was evacuated under reduced pressure and purged three times with an atmosphere of $N_2$. To the flask was then added 20.4 g of 20% $Pd(OH)_2$ on carbon. The flask was again evacuated under reduced pressure and purged three times with an atmosphere of $N_2$, and then three times with $H_2$. The reaction was stirred under an atmosphere of $H_2$ overnight, then filtered through a pad of celite, rinsing with EtOAc followed by MeOH. The filtrate was concentrated to provide F-3 as a white solid. Data for F-3: LC/MS: rt=0.81 & 1.01 min (see two conformers under these conditions); m/z (M+H)=286.2 found; 286.3 required.

6-fluoro-2-{(5R)-5-methyl-4-[2-(2H-1,2,3-triazol-2-yl)benzoyl]-1,4-diazepan-1-yl}quinazoline (F-4)

To 3.0 g (10.5 mmol) F-3 in 50 mL DMF was added 4.40 mL (31.5 mmol) triethylamine and 1.92 g (10.5 mmol) B-3 and the mixture was heated in an oil bath at 75° C. for 4 h, the temperature of the bath was decreased to 50° C. and the reaction was stirred overnight at that temperature. After cooling to room temperature, the reaction was diluted with EtOAc, washed with saturated aqueous $NaHCO_3$, water, brine and dried over $MgSO_4$. Following concentration by rotary evaporation, the residue was purified by flash column chromatography (hexanes/EtOAc) to provide F-4 as a yellow solid. Data for F-4: LC/MS: rt=1.88 & 1.95 min (see two conformers under these conditions); m/z (M+H)=432.2 found; 432.2 required; HRMS (APCI) m/z (M+H) 432.1949 found; 432.1943 required.

SCHEME G

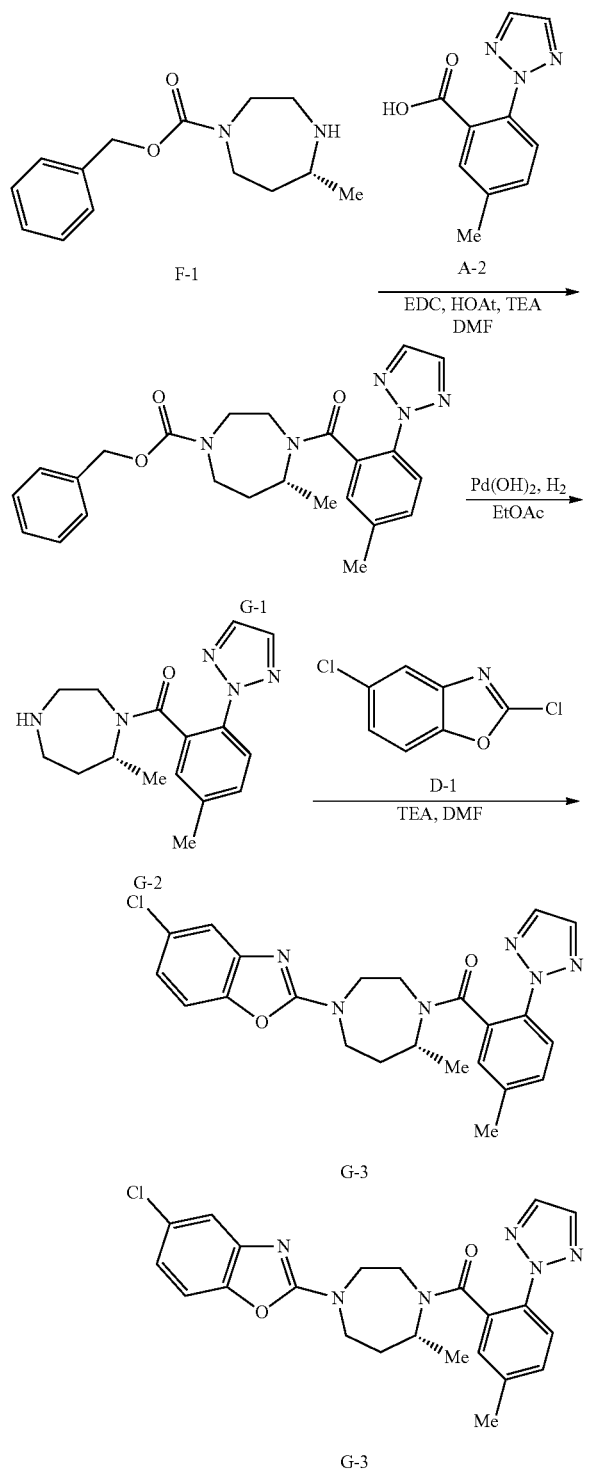

benzyl (5R)-5-methyl-4-[5-methyl-2-(2H-1,2,3-tria-
zol-2-yl)benzoyl]-1,4-diazepane-1-carboxylate (G-1)

To a solution of 22.3 g (78 mmol) of the hydrochloride salt of F-1, 15.9 g (78 mmol) A-2, 12.8 g (94 mmol) 1-hydroxy-7-azabenzotriazole, and 43.1 mL (392 mmol) N-methylmorpholine in 300 mL of DMF was added 22.5 g (118 mmol) EDC and the reaction was stirred overnight at room temperature. The reaction was partitioned between EtOAc and saturated aqueous $NaHCO_3$, washed with water, brine, dried over $MgSO_4$, and concentrated by rotary evaporation. The residue was purified by column chromatography on silica gel (EtOAc/hexanes) to provide G-1 as a colorless gum. Data for G-1: LC/MS: rt=2.22 min; m/z (M+H)=434.2 found; 434.2 required.

(7R)-7-methyl-1-[5-methyl-2-(2H-1,2,3-triazol-2-yl)benzoyl]-1,4-diazepane (G-2)

A round bottom flask containing a solution of 29.6 g (68.3 mmol) G-1 in 300 mL EtOAc and 200 ml MeOH was evacuated under reduced pressure and purged three times with an atmosphere of $N_2$. To the flask was then added 2.4 g of 20% $Pd(OH)_2$ on carbon. The flask was again evacuated under reduced pressure and purged three times with an atmosphere of $N_2$, and then three times with $H_2$. The reaction was stirred under an atmosphere of $H_2$ for three days, then filtered through a pad of celite, rinsing with EtOAc followed by MeOH. The filtrate was concentrated to provide G-2 as a white foam. Data for G-2: LC/MS: rt=0.96 & 1.13 min (see two conformers under these conditions); m/z (M+H)=300.0 found; 300.2 required.

5-chloro-2-{(5R)-5-methyl-4-[5-methyl-2-(2H-1,2,3-triazol-2-yl)benzoyl]-1,4-diazepan-1-yl}-1,3-benzoxazole (G-3)

To 21.0 g (70.1 mmol) G-2 in 250 mL DMF was added 29.3 mL (210 mmol) triethylamine and 13.2 g (70.1 mmol) D-1 and the mixture was heated in an oil bath at 75° C. for 2 h. After cooling to room temperature, the reaction was diluted with EtOAc, washed with saturated aqueous $NaHCO_3$, water, brine and dried over $MgSO_4$. Following concentration by rotary evaporation, the residue was purified by flash column chromatography (hexanes/EtOAc) to provide a gum. The gum was stirred in a mixture of 150 ml EtOAc and 300 ml hexanes overnight. Filtration provided G-3 as a white solid. Data for G-3: LC/MS: rt=2.29 min; m/z (M+H)=451.1 found; 451.2 required; HRMS (APCI) m/z (M+H) 451.1631 found; 451.1644 required.

SCHEME H

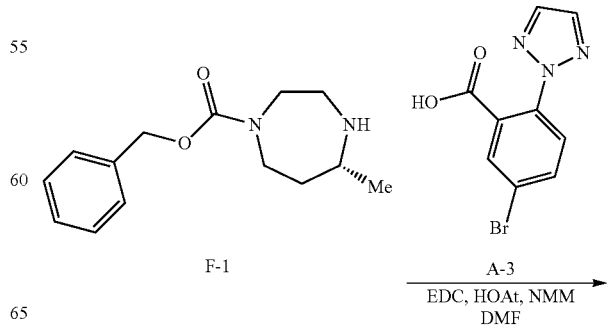

-continued

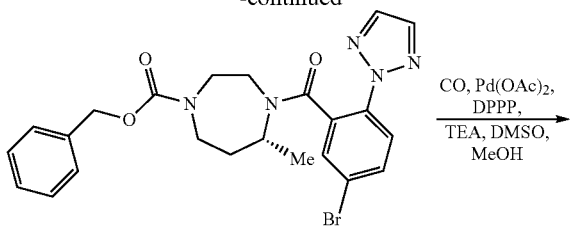

H-1

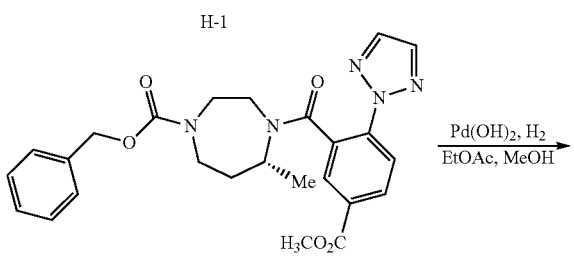

H-2

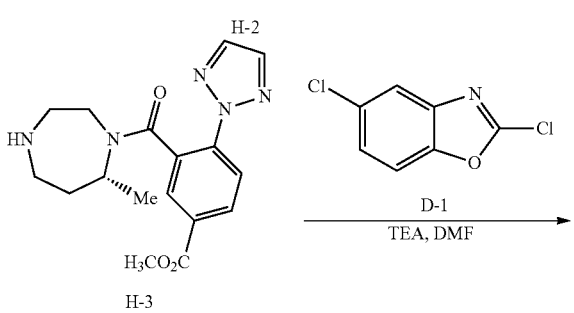

H-3

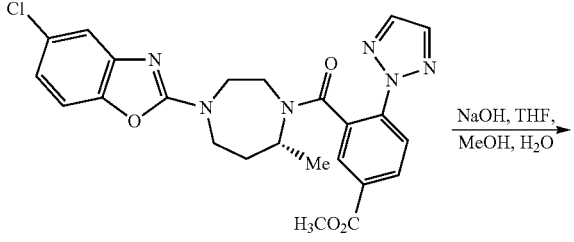

H-4

Cl
<br>
(structure H-5)

H-5 benzyl (5R)-4-[5-bromo-2-(2H-1,2,3-triazol-2-yl)
benzoyl]-5-methyl-1,4-diazepane-1-carboxylate
(H-1)

To a solution of 2.5 g (8.8 mmol) of the hydrochloride salt of F-1, 2.35 g (8.8 mmol) A-3, 1.43 g (10.5 mmol) 1-hydroxy-7-azabenzotriazole, and 4.83 mL (43.9 mmol) N-methylmorpholine in 35 mL of DMF was added 2.52 g (13.2 mmol) EDC and the reaction was stirred overnight at room temperature. The reaction was partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide H-1 as a white solid. Data for H-1: LC/MS: rt=2.28 & 2.34 min (see two conformers under these conditions); m/z (M+H)=498.1 found; 498.1 required.

benzyl (5R)-4-[5-(methoxycarbonyl)-2-(2H-1,2,3-triazol-2-yl)benzoyl]-5-methyl-1,4-diazepane-1-carboxylate (H-2)

Carbon monoxide was bubbled through a solution of 2.63 g (5.3 mmol) of H-1, 118 mg (0.53 mmol) palladium(II) acetate, 218 mg (0.53 mmol) 1,3-bis(diphenylphosphino)-propane, and 2.21 mL (15.8 mmol) triethylamine in 20 mL of methanol and 10 ml of DMSO at 80° C. for 10 minutes. The reaction was then placed under a balloon of carbon monoxide and stirred at 80° C. overnight. The reaction was partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide H-2 as a colorless gum. Data for H-2: LC/MS: rt=2.10 & 2.16 min (see two conformers under these conditions); m/z (M+H)=478.1 found; 478.2 required.

methyl 3-{[(7R)-7-methyl-1,4-diazepan-1-yl]carbonyl}-4-(2H-1,2,3-triazol-2-yl)benzoate (H-3)

A round bottom flask containing a solution of 750 mg (1.57 mmol) H-2 in 100 mL EtOAc and 20 ml MeOH was evacuated under reduced pressure and purged three times with an atmosphere of N$_2$. To the flask was then added 1.1 g of 20% Pd(OH)$_2$ on carbon. The flask was again evacuated under reduced pressure and purged three times with an atmosphere of N$_2$, and then three times with H$_2$. The reaction was stirred under an atmosphere of H$_2$ for 24 hours, then filtered through a pad of celite, rinsing with EtOAc followed by MeOH. The filtrate was concentrated to provide H-3 as a colorless gum. Data for H-3: LC/MS: rt=1.01 & 1.13 min (see two conformers under these conditions); m/z (M+H)=344.1 found; 344.2 required.

methyl 3-{[(7R)-4-(5-chloro-1,3-benzoxazol-2-yl)-7-methyl-1,4-diazepan-1-yl]carbonyl}-4-(2H-1,2,3-triazol-2-yl)benzoate (H-4)

To 540 mg (1.57 mmol) H-3 in 10 mL DMF was added 0.22 mL (1.57 mmol) triethylamine and 310 mg (1.65 mmol) D-1 and the mixture was heated in an aluminum block at 50° C. overnight. After cooling to room temperature, the reaction was diluted with EtOAc, washed with saturated aqueous NaHCO$_3$, water, brine and dried over MgSO$_4$. Following concentration by rotary evaporation, the residue was purified by flash column chromatography (hexanes/EtOAc) to provide H-4 as a white solid. Data for H-4: LC/MS: rt=2.24 min; m/z (M+H)=495.1 found; 495.2 required. HRMS (APCI) m/z (M+H) 495.1561 found; 495.1542 required.

3-{[(7R)-4-(5-chloro-1,3-benzoxazol-2-yl)-7-methyl-1,4-diazepan-1-yl]carbonyl}-4-(2H-1,2,3-triazol-2-yl)benzoic acid (H-5)

To 120 mg (0.24 mmol) H-4 in 20 mL each of MeOH/THF/H$_2$O was added 1.94 mL (1.94 mmol) 1M aqueous sodium hydroxide solution and the mixture was stirred overnight at room temperature. The reaction was concentrated to remove organic solvents then diluted with EtOAc, washed with 1M NaOH three times. Aqueous layers were acidified with 1M HCl, washed three times with EtOAc, organics were combined and washed with water, brine and dried over MgSO$_4$. Following concentration by rotary evaporation, the residue was suspended in Et2O/hexanes and concentrated to provide H-5 as a white solid. Data for H-5: LC/MS: rt=1.94 min; m/z (M+H)=481.1 found; 481.1 required. HRMS (APCI) m/z (M+H) 481.1409 found; 481.1386 required.

SCHEME I

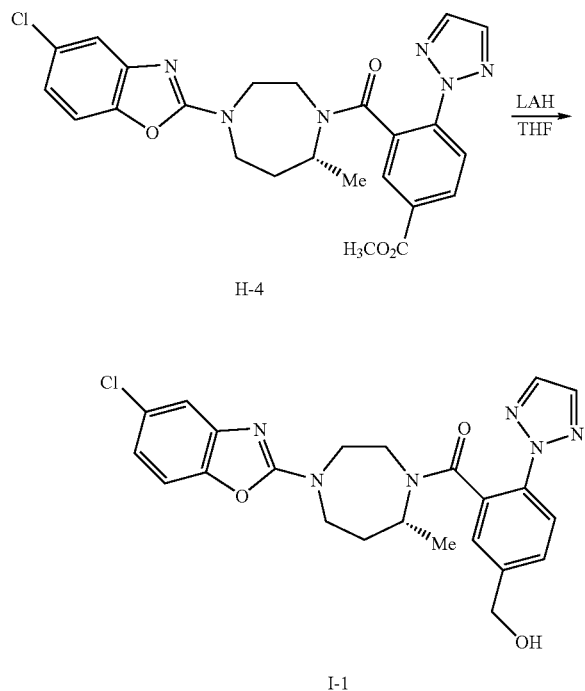

[3-{[(7R)-4-(5-chloro-1,3-benzoxazol-2-yl)-7-methyl-1,4-diazepan-1-yl]carbonyl}-4-(2H-1,2,3-triazol-2-yl)phenyl]methanol (I-1)

To 400 mg (0.81 mmol) H-4 in 10 mL of THF was added 0.70 mL (1.62 mmol) 2.3M lithium aluminum hydride solution in THF and the mixture was stirred for 30 minutes at room temperature. The reaction was quenched with water then diluted with EtOAc, washed with 1M HCl, water, brine and dried over MgSO$_4$. Following concentration by rotary evaporation, the residue was purified by flash column chromatography (hexanes/EtOAc), concentrated, suspended in Et2O/hexanes and concentrated again to provide I-1 as a white solid. Data for I-1: LC/MS: rt=1.86 min; m/z (M+H)= 467.1 found; 467.2 required. HRMS (APCI) m/z (M+H) 467.1623 found; 467.1593 required.

SCHEME J

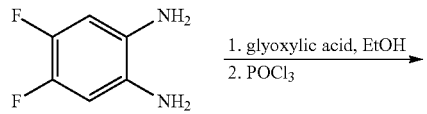

1. glyoxylic acid, EtOH
2. POCl$_3$

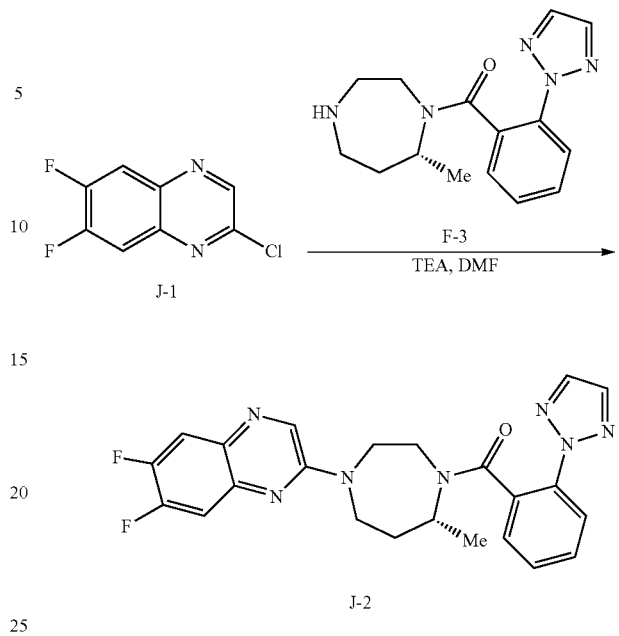

2-Chloro-6,7-Difluroquinoxaline (J-1)

A solution of 4,5-difluoro-1,2-phenylenediamine (3 g, 20.82 mmol) in EtOH (100 ml) was treated with glyoxylic acid (2.34 mL, 21.02 mmol, 50 wt % in water) and heated to reflux for 3 h. The mixture was cooled to 0° C. and the solid was collected by filtration. This material was diluted with POCl3 (29.1 ml, 312 mmol) and stirred at reflux for 1 h. The reflux condenser was removed and a stream of N$_2$ gas was blown over the mixture as it was allowed to concentrate. The residue was diluted with DCM, cooled to 0° C. and 5% aqueous Na$_2$CO$_3$ was added slowly. The mixture was poured into a separatory funnel and the layers were separated. The organic phase was washed with 5% aqueous Na$_2$CO$_3$, dried over Na$_2$SO$_4$, filtered and concentrated. The crude material was dissolved in CHCl$_3$, treated with 12 g of silica gel and concentrated to a fine powder. This was loaded on silica gel and purified by isocratic elution (10% EtOAc in DCM) to yield J-1 as an off-white solid. Data for J-1: $^1$H NMR (500 MHz. CDCl$_3$): δ 8.8 (s, 1H), 7.9 (m, 1H), 7.8 (m, 1H) ppm.

6,7-difluoro-2-{(5R)-5-methyl-4-[2-(2H-1,2,3-triazol-2-yl)benzoyl]-1,4-diazepan-1-yl}quinoxaline (J-2)

To 711 mg (2.5 mmol) F-3 in 10 mL DMF was added 1.04 mL (7.5 mmol) triethylamine and 500 mg (2.5 mmol) J-1 and the mixture was heated in an aluminum block at 75° C. for five hours. After cooling to room temperature, the reaction was diluted with EtOAc, washed with saturated aqueous NaHCO$_3$, water, brine and dried over MgSO$_4$. Following concentration by rotary evaporation, the residue was purified by flash column chromatography (hexanes/EtOAc) concentrated, suspended in Et2O/hexanes and concentrated again to provide J-2 as a yellow solid. Data for J-2: LC/MS: rt=2.20 min; m/z (M+H)=450.0 found; 450.2 required. HRMS (APCI) m/z (M+H) 450.1862 found; 450.1848 required.

SCHEME K

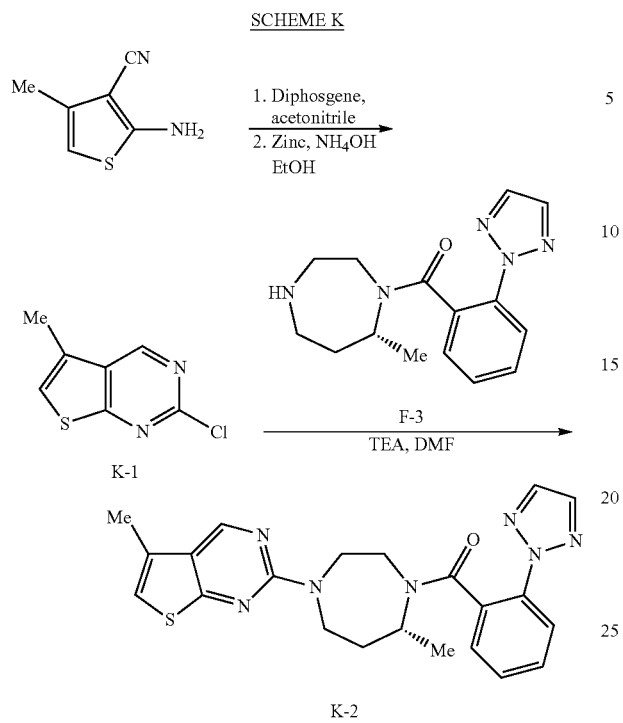

SCHEME L

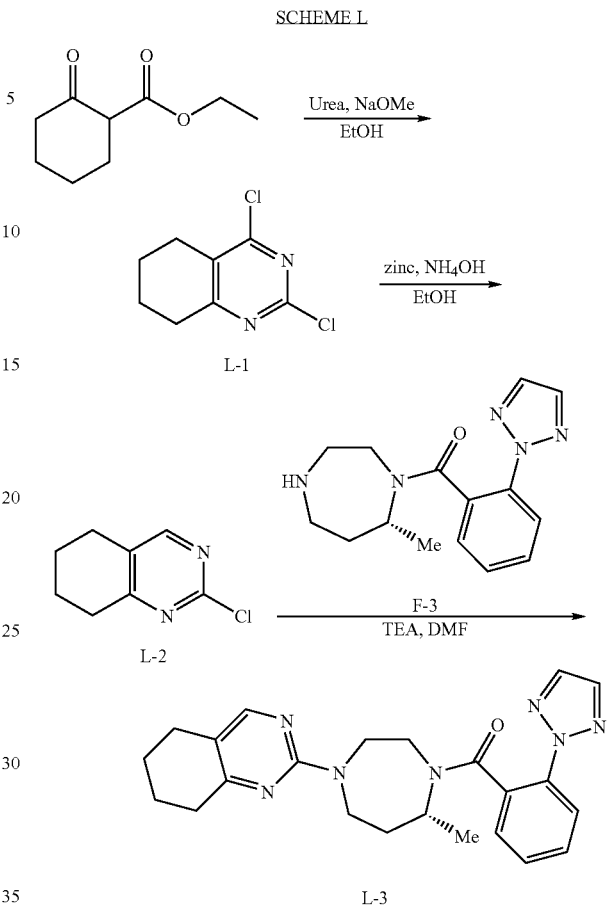

2-chloro-5-methylthieno[2,3-d]pyrimidine (K-1)

To 1.5 g (10.9 mmol) of 2-amino-4-methylthiophene-3-carbonitrile in acetonitrile (9 mL) was added 2.0 mL (16.3 mmol) of diphosgene and the mixture was heated in an sealed tube at 100° C. for 15 hours. After cooling to room temperature, the reaction was poured into water slowly and partitioned between water and EtOAc. The organic phase was washed with saturated NH$_4$Cl, dried over MgSO$_4$ and concentrated. The residual yellow solid was dissolved in ethanol (30 mL) and to this suspension was added 2.4 g (36.1 mmol) of zinc dust and 3.1 mL (22.6 mmol) of ammonium hydroxide and the reaction was heated to 78° C. for 1 hour. After cooling the reaction mixture to ambient temperature, the mixture was filtered through celite, partitioned between EtOAc and water, and extracted with EtOAc (2×100 mL). The organic phase was dried over MgSO4 and concentrated and the residue was purified by flash column chromatography (EtOAc/hexanes) to afford K-1 as an off-white solid. Data for K-1: LC/MS: rt=2.03 min; m/z (M+H)=185.1 found; 185.0 required.

5-methyl-2-{(5R)-5-methyl-4-[2-(2H-1,2,3-triazol-2-yl)benzoyl]-1,4-diazepan-1-yl}thieno[2,3-d]pyrimidine (K-2)

To 27 mg (0.15 mmol) of 2-chloro-5-methylthieno[2,3-d]pyrimidine and 42 mg (0.15 mmol) of F-3 in DMF (1.0 mL) was added 0.1 mL (0.73 mmol) of triethylamine and the mixture was heated at 90° C. for 15 hours. After cooling to room temperature, the reaction was poured into water and partitioned between water and EtOAc. The organic phase was washed with saturated NH$_4$Cl, dried over MgSO$_4$ and concentrated. The residue was purified by flash column chromatography (EtOAc/hexanes) to afford K-2 as an off-white foamy solid. Data for K-2: LC/MS: rt=2.68 min; m/z (M+H)= 434.1 found; 434.2 required; HRMS m/z (M+H)=434.1769 found; 434.1764 required.

2,4-dichloro-5,6,7,8-tetrahydroquinazoline (L-1)

To 10.0 g (58.8 mmol) of ethyl 2-oxocyclohexanecarboxylate in ethanol (200 mL) was added 29.4 mL (118 mmol) of sodium methoxide and 4.6 g (76 mmol) of urea and the mixture was heated at 80° C. for 15 hours. After cooling to room temperature, a white solid was filtered off and washed several times with cold diethyl ether. After drying under high vacuum, the white solid was dissolved in neat phosphorous oxychloride (77 mL) and heated to 120° C. for 1 hour. The reaction was cooled to room temperature and the excess phosphorous oxychloride was removed via rotary evaporation. The residue was partitioned between EtOAc (400 mL) and water (200 mL) and the organic phase was washed sequentially with saturated NaHCO$_3$ (200 mL) and brine (200 mL). The organic phase was dried over MgSO$_4$ and concentrated. The residue was purified by flash column chromatography (EtOAc/hexanes) to afford L-1 as a slightly yellow solid. Data for L-1: LC/MS: rt=2.49 min; m/z (M+H)=203.1 found; 203.0 required.

2-chloro-5,6,7,8-tetrahydroquinazoline (L-2)

4.7 g (23.1 mmol) of L-1 was de-chlorinated in an analogous fashion described for K-1 to yield L-2 as a white solid. Data for L-2: LC/MS: rt=1.92 min; m/z (M+H)=169.2 found; 169.1 required.

2-{(5R)-5-methyl-4-[2-(2H-1,2,3-triazol-2-yl)benzoyl]-1,4-diazepan-1-yl}-5,6,7,8-tetrahydroquinazoline (L-3)

284 mg (1.68 mmol) of L-2 and 400 mg (1.40 mmol) of F-3 were coupled in an analogous fashion described for K-2 to yield L-3 as a white solid. Data for L-3: LC/MS: rt=1.73 min; m/z (M+H)=418.1 found; 418.2 required; HRMS m/z (M+H)= 418.2348 found; 418.2355 required.

SCHEME M

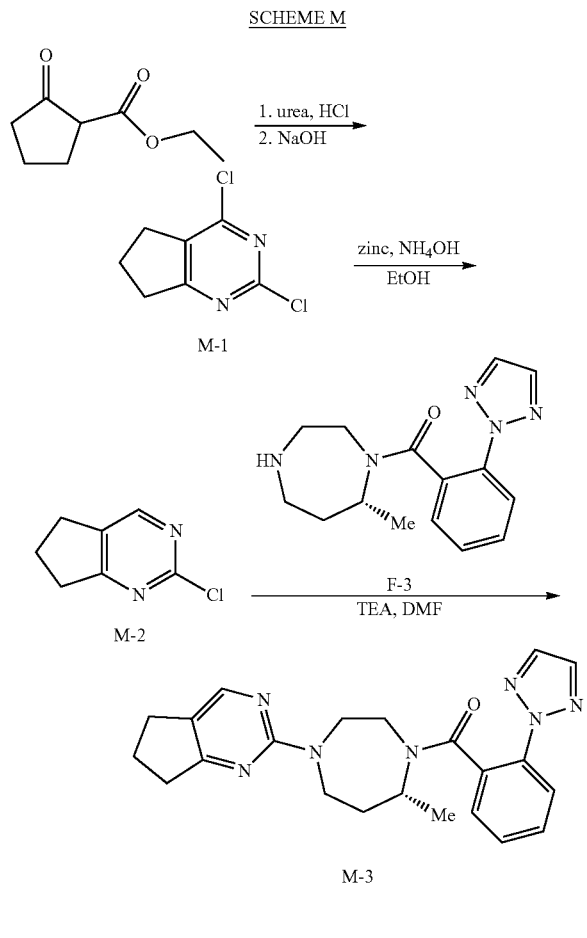

2,4-dichloro-6,7-dihydro-5H-cyclopenta[d]pyrimidine (M-1)

To 10 g (64.0 mmol) of ethyl 2-oxocyclopentanecarboxylate in ethanol (130 mL) was added 0.80 mL (9.6 mmol) of concentrated HCl and 5.8 g (96.0 mmol) of urea and the mixture was heated at 80° C. for 4 hours. After cooling to room temperature, a solid was filtered off and washed several times with cold diethyl ether. After drying under high vacuum, the white solid was dissolved in 1N NaOH (100 mL) and heated to 110° C. for 1 hour. The reaction was cooled to room temperature and the acidified with 3N HCl to pH 2 and a solid was collected by filtration. The solid was washed with cold diethyl ether and dried under high vacuum overnight (Procedure slightly modified from *Eur. J. Med. Chem.* 1980, 15, 317-322). After drying under high vacuum, the solid was dissolved in neat phosphorous oxychloride (55 mL) and heated to 120° C. for 1 hour. The reaction was cooled to room temperature and the excess phosphorous oxychloride was removed via rotary evaporation. The residue was partitioned between EtOAc (400 mL) and water (200 mL) and the organic phase was washed sequentially with saturated NaHCO$_3$ (200 mL) and brine (200 mL). The organic phase was dried over MgSO$_4$ and concentrated. The residue was purified by flash column chromatography (EtOAc/hexanes) to afford M-1 as a white solid. Data for M-1: LC/MS: rt=2.40 min; m/z (M+H)= 189.1 found; 189.0 required.

2-chloro-6,7-dihydro-5H-cyclopenta[d]pyrimidine (M-2)

4.2 g (22.2 mmol) of M-1 was de-chlorinated in an analogous fashion described for K–1 to yield M-2 as a white solid. Data for M-2: LC/MS: rt=1.22 min; m/z (M+H)=155.1 found; 155.0 required.

2-{(5R)-5-methyl-4-[2-(2H-1,2,3-triazol-2-yl)benzoyl]-1,4-diazepan-1-yl}-6,7-dihydro-5H-cyclopenta[d]pyrimidine (M-3)

32.5 mg (0.21 mmol) of M-2 and 30 mg (0.105 mmol) of F-3 were coupled in an analogous fashion described for K-2 to yield M-3 as a white solid. Data for M-3: LC/MS: rt=1.88 min; m/z (M+H)=404.4 found; 404.2 required; HRMS m/z (M+H)=404.2204 found; 404.2199 required.

SCHEME N

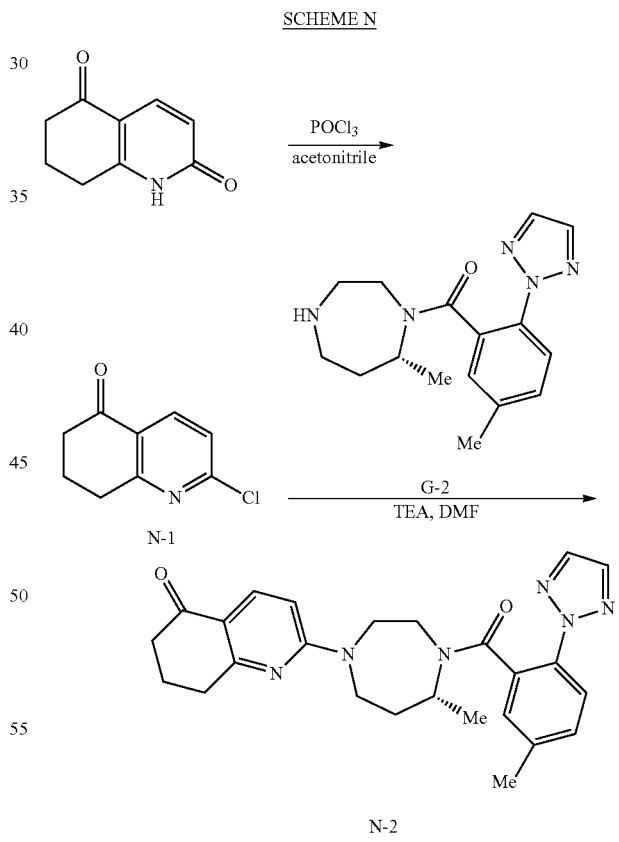

2-chloro-7,8-dihydroquinolin-5(6H)-one(N-1)

To 200 mg (1.23 mmol) of 7,8-dihydroquinoline-2,5(1H, 6H)-dione in acetonitrile (6.1 mL) was added 1.14 mL (12.3 mmol) of phosphorous oxychloride and the mixture was heated at 65° C. for 3 hours. The reaction was cooled to room temperature and the excess phosphorous oxychloride was removed via rotary evaporation. The residue was partitioned between EtOAc (400 mL) and water (200 mL) and the organic phase was washed sequentially with saturated NaHCO₃ (200 mL) and brine (200 mL). The organic phase was dried over MgSO₄ and concentrated to afford N-1 as a beige solid. Data for N-1: LC/MS: rt=1.64 min; m/z (M+H)=182.1 found; 182.0 required.

2-{(5R)-5-methyl-4-[5-methyl-2-(2H-1,2,3-triazol-2-yl)benzoyl]-1,4-diazepan-1-yl}-7,8-dihydroquinolin-5(6H)-one (N-2)

36.4 mg (0.21 mmol) of N-1 and 50 mg (0.105 mmol) of G-2 were coupled in an analogous fashion described for K-2 to yield N-2 as a white solid. Data for N-2: LC/MS: rt=1.88 min; m/z (M+H)=445.1 found; 445.2 required; HRMS m/z (M+H)=445.2357 found; 445.2352 required.

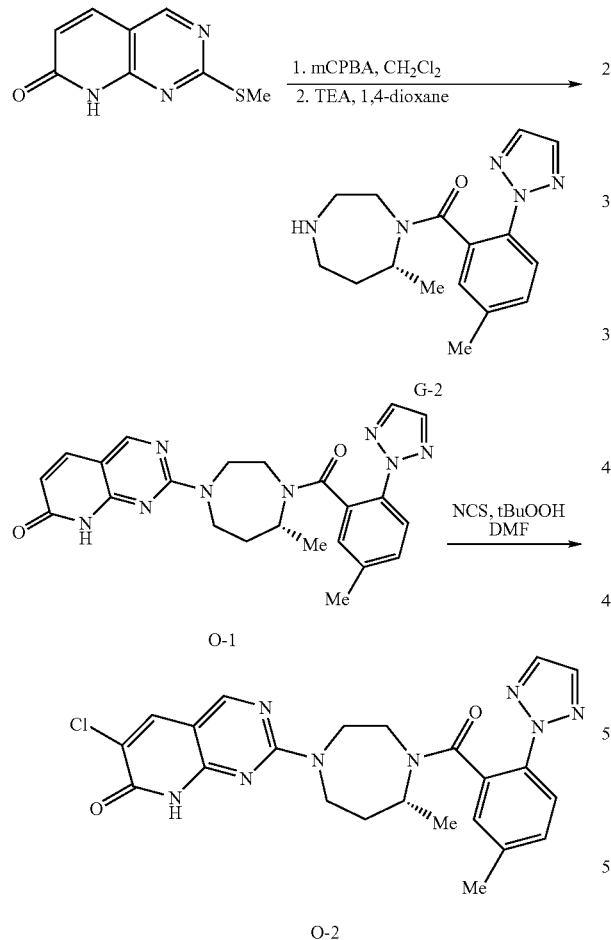

O-1

2-{(5R)-5-methyl-4-[5-methyl-2-(2H-1,2,3-triazol-2-yl)benzoyl]-1,4-diazepan-1-yl}pyrido[2,3-d]pyrimidin-7(8H)-one (O-1)

To 670 mg (3.47 mmol) of 2-(methylthio)pyrido[2,3-d]pyrimidin-7(8H)-one (synthesized via procedures found in *J. Med. Chem.* 2000, 43, 4606-4616) in CH₂Cl₂ (17 mL) was added 1.55 g (6.93 mmol) of mCPBA and the mixture stirred at ambient temperature for 1 hour. The reaction was concentrated directly and redissolved in dioxane (10 mL). To this solution was added 675 mg (2.25 mmol) of G-2 and 2.4 mL (17.3 mmol) of triethylamine. The reaction was heated to 100° C. for 6 hours. The reaction was cooled to ambient temperature, quenched with saturated NH₄Cl and extracted with EtOAc (4×20 mL). The organic phase was dried over MgSO₄ and concentrated. The residue was purified by flash column chromatography (EtOAc/hexanes) to afford O-1 as a solid. Data for O-1: LC/MS: rt=2.01 min; m/z (M+H)=445.4 found; 445.2 required.

6-chloro-2-{(5R)-5-methyl-4-[5-methyl-2-(2H-1,2,3-triazol-2-yl)benzoyl]-1,4-diazepan-1-yl}pyrido[2,3-d]pyrimidin-7(8H)-one (O-2)

To 660 mg (1.49 mmol) of O-1 in DMF (7.4 mL) was added 347 mg (2.60 mmol) of N-chlorosuccinimide (NCS) and 108 mg (0.45 mmol) of benzoyl peroxide and the mixture stirred at ambient temperature for 24 hours. The reaction was diluted with EtOAc (75 mL) and washed with water (4×30 mL). The organic phase was dried over MgSO₄ and concentrated. The residue was purified by flash column chromatography (EtOAc/hexanes) to afford O-2 as a white solid. Data for O-2: LC/MS: rt=2.19 min; m/z (M+H)=479.1 found; 479.2 required; HRMS m/z (M+H)=479.1748 found; 479.1710 required.

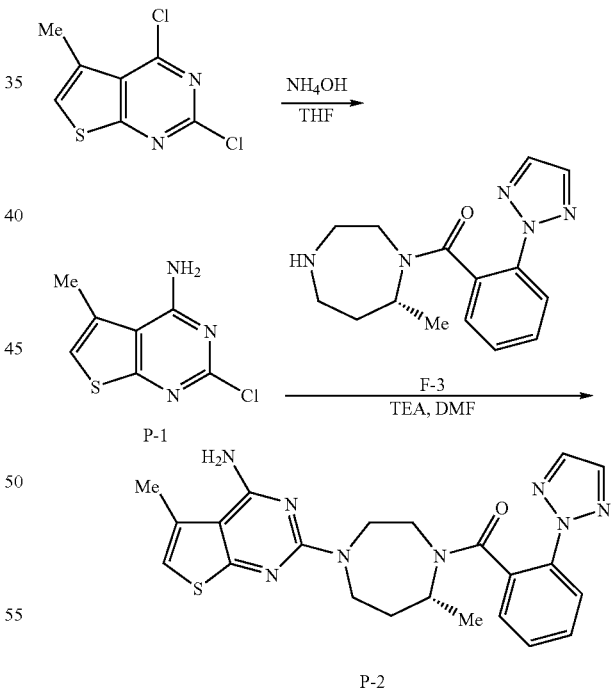

2-chloro-5-methylthieno[2,3]pyrimidin-4-amine (P-1)

To a solution of 2,4-dichloro-5-methylthieno[2,3]pyrimidine (0.20 g, 0.9 mmol) in 5 mL THF was added ammonium hydroxide (0.57 g, 4.5 mmol) and stirred at room temperature over two days. The system was then partitioned between EtOAc and water, dried over MgSO$_4$ concentrated and purified using normal phase chromatography (0->75% EtOAc/hexanes) to afford P-1 as a bone powder. Data for P-1: LC/MS: rt=1.48 min; m/z (M+H)=200.1 found; 200.1 required.

5-methyl-2-(4-[2-(2H-1,2,3-triazol-2-yl)benzoyl]-1,4-diazepan-1-yl}thieno[2,3]pyrimidin-4-amine (P-2)

To a solution of P-1 (0.09 g, 0.49 mmol) and F-3 (0.15 g, 0.54 mmol) in 2 mL DMF was added triethylamine (0.25 g, 2.5 mmol) and the system was heated in the microwave at 185° C. for 40 minutes. The system was then partitioned between EtOAc and water, dried over MgSO$_4$ concentrated and purified using normal phase chromatography (EtOAc/hexanes) to afford P-2 as a white foam. Data for P-2: LC/MS: rt=1.45 min; m/z (M+H)=449.1 found; 449.1 required. HRMS m/z (M+H)=449.1869 found; 449.1867 required.

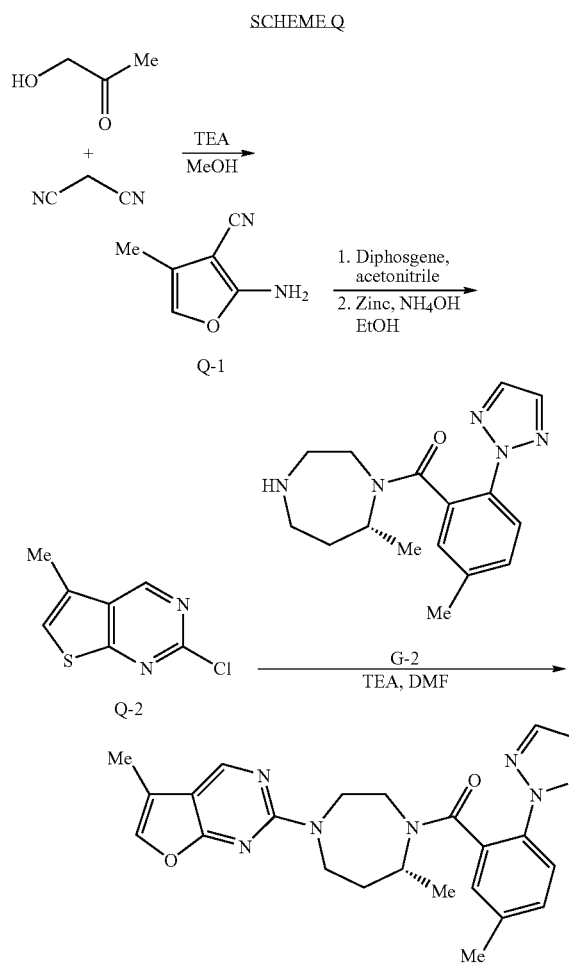

2-amino-4-methyl-3-furonitrile (Q-1)

To a solution of hydroxyacetone (1.0 g, 13.5 mmol) in 45 mL MeOH was added a solution of malonitrile (0.9 g, 13.5 mmol) in TEA (1.36 g, 13.5 mmol) and 10 mL MeOH. After stirring overnight at room temperature, the solvents were removed by rotary evaporation to give Q-1 as a brown semi-solid. Data for Q-1: $^1$H NMR (500 MHz, CDCl$_3$) δ 2.01 (s, 3H), 4.71 (br s, 2H), 6.57 (s, 1H).

2-chloro-5-methylfuro[2,3]pyrimidine (Q-2)

To a solution of Q-1 (1.6 g, 13.1 mmol) in 13 mL ACN in a sealed tube was added diphosgene (3.9 g, 19.6 mmol) and heated to 95° C. overnight. The system was cooled to ambient temperature and the contents were partitioned between EtOAc/DCM and water, dried over MgSO$_4$, and concentrated to afford a brown oil. To a solution of this brown oil (1.0 g, 4.9 mmol) in 30 mL EtOH was added zinc dust (2.6 g, 39.4 mmol), ammonium hydroxide (3.0 g, 24.6 mmol) and heated to 78° C. for 0.5 h. The system was then cooled and filtered through a pad of celite. The filtrate was then partitioned between EtOAc and water, dried over MgSO$_4$, concentrated and purified via normal phase chromatography (EtOAc/hexanes) to afford Q-2 as a yellow crystalline solid. Data for Q-2: LC/MS: rt=1.65 min; m/z (M+H)=169.0 found; 169.0 required.

5-methyl-2-{(5R)-5-methyl-4-[5-methyl-2-(2H-1,2,3-triazol-2-yl)benzoyl]-1,4-diazepan-1-yl}furo[2,3]pyrimidine (Q-3)

To a solution of Q-2 (0.02 g, 0.14 mmol) and G-2 (0.04 g, 0.14 mmol) in 2 mL DMF was added triethylamine (0.07 g, 0.71 mmol) and the system was heated in the microwave at 120° C. for 25 minutes. The reaction contents were filtered and purified by reverse phase conditions (5% 95% 0.1% TFA in water: 0.1% TFA in ACN) followed by free basing with saturated sodium carbonate to afford Q-3 as a bone foam. Data for Q-3: LC/MS: rt=2.55 min; m/z (M+H)=432.3 found; 432.4 required. HRMS m/z (M+H)=432.2144 found; 432.2143 required.

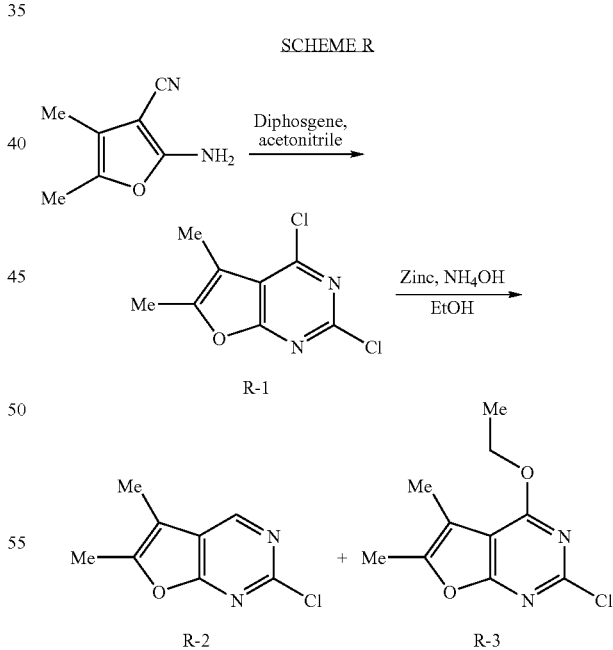

2-chloro-5,6-dimethylfuro[2,3]pyrimidine (R-2) and 2-chloro-4-ethoxy-5,6-dimethylfuro[2,3]pyrimidine (R-3)

To a solution of 2-amino-4,5-dimethyl-3-furonitrile (1.0 g, 7.3 mmol) in 7 mL ACN in a sealed tube was added diphosgene (3.9 g, 19.6 mmol) and heated to 95° C. overnight. The system was cooled to ambient temperature and the contents were partitioned between EtOAc/DCM and water, dried over MgSO$_4$, concentrated and purified using normal phase chromatography (0->100% EtOAc/hexanes) to afford R-1 as a pink solid. To this solid (0.23 g, 1.0 mmol) in 8 mL EtOH was added Zinc dust (0.56 g, 8.6 mmol), ammonium hydroxide (0.67 g, 5.4 mmol) and heated to 78° C. overnight. The system was then cooled and filtered through a pad of celite. The filtrate was then partitioned between EtOAc and water, dried over MgSO$_4$ and concentrated to afford a mixture of R-2 and R-3 as a tan solid that was carried on as is. Data for R-2: LC/MS: rt=2.04 min; m/z (M+H)=183.0 found; 183.0 required. Data for R-3: LC/MS: rt=3.19 min; m/z (M+H)= 227.1 found; 227.0 required.

purified using normal phase chromatography (EtOAc/hexanes) to afford a white crystalline powder. To a solution of this white crystalline powder (0.37 g, 1.7 mmol) in 12 mL EtOH was added Zinc dust (0.9 g, 13.9 mmol), ammonium hydroxide (1.1 g, 8.7 mmol) and heated to 78° C. for 0.5 h. The system was then cooled and filtered through a pad of celite. The filtrate was partitioned between EtOAc and water, dried over MgSO$_4$, and concentrated to afford S-2 as a yellow solid. Data for S-2: LC/MS: rt=1.31 min; m/z (M+H)=183.1 found; 183.0 required

SCHEME T

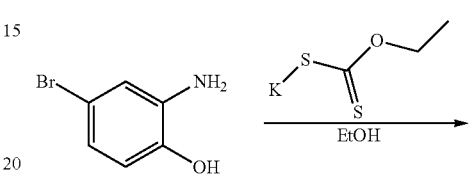

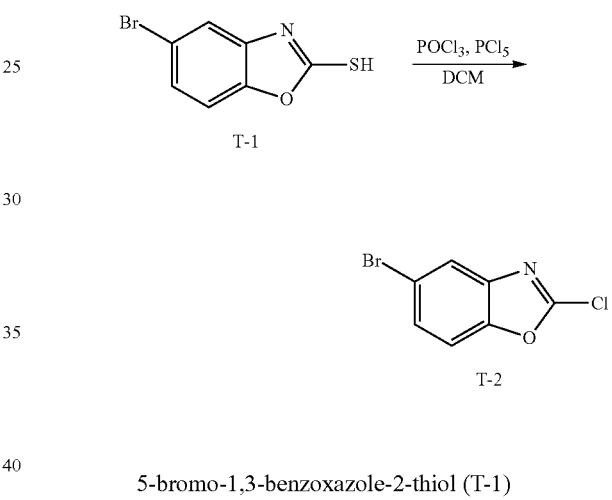

5-bromo-1,3-benzoxazole-2-thiol (T-1)

SCHEME S

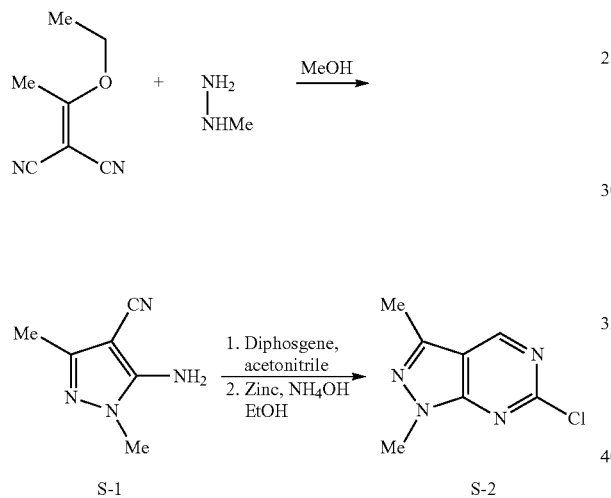

5-amino-1,3-dimethylpyrazole-4-carbonitrile (S-1)

To a solution of (1-ethoxyethylidene)malonitrile (4.0 g, 29.4 mmol) in 75 mL MeOH was added methylhydrazine (1.3 g, 29.4 mmol) and the system was stirred at 65° C. for 2 h. The reaction contents were pored into a flask containing 1N HCl. After stirring overnight at room temperature, the solvents were removed by rotary evaporation to give a brown semi-solid. This material was partitioned between EtOAc and water, dried over MgSO$_4$, and concentrated to afford S-1 as a tan powder. Data for S-1: $^1$H NMR (500 MHz, CDCl$_3$) δ 2.21 (s, 3H), 3.55 (s, 3H), 4.13 (br s, 2H).

6-chloro-1,3-dimethylpyrazolo[3,4]pyrimidine (S-2)

To a solution of S-1 (1.0 g, 7.3 mmol) in 7 mL ACN in a sealed tube was added diphosgene (2.1 g, 11.0 mmol) and heated to 95° C. overnight. The system was cooled to ambient temperature and the contents were partitioned between EtOAc/DCM and water, dried over MgSO$_4$, concentrated and To a solution of 2-amino-4-bromophenol (3.0 g, 15.9 mmol) in 45 mL EtOH was added potassium ethylxanthate (5.1 g, 31.9 mmol) and the system was stirred at 80° C. for 3 h, cooled to room temperature and stirred overnight. The solvent was removed in vacuo and then dissolved in water and acidified with acetic acid resulting in precipitate formation. This precipitate was collected by filtration which afforded T-1 as a grayish white powder. Data for T-1: LC/MS: rt=2.17 min; m/z (M+H)=230.0 found; 230.0 required.

5-bromo-2,chloro-1,3-benzoxazole (T-2)

To a solution of T-1 (1.8 g, 7.8 mmol) in 6 mL DCM was added phosphorous oxychloride (6.0 g, 39.1 mmol) followed by phosphorous pentachloride (2.4 g, 11.7 mmol) and the system was stirred overnight at room temperature. The solvent was removed in vacuo and the reaction contents were partitioned between DCM, a saturated solution of sodium bicarbonate, and water. The organic layer was dried over Na$_2$SO$_4$, concentrated and purified using normal phase chromatography (EtOAc/Hexanes) to afford T-2 as a white solid. Data for T-2: LC/MS: rt=2.37 min; m/z (MS)=232.9 found; 232.9 required.

SCHEME U

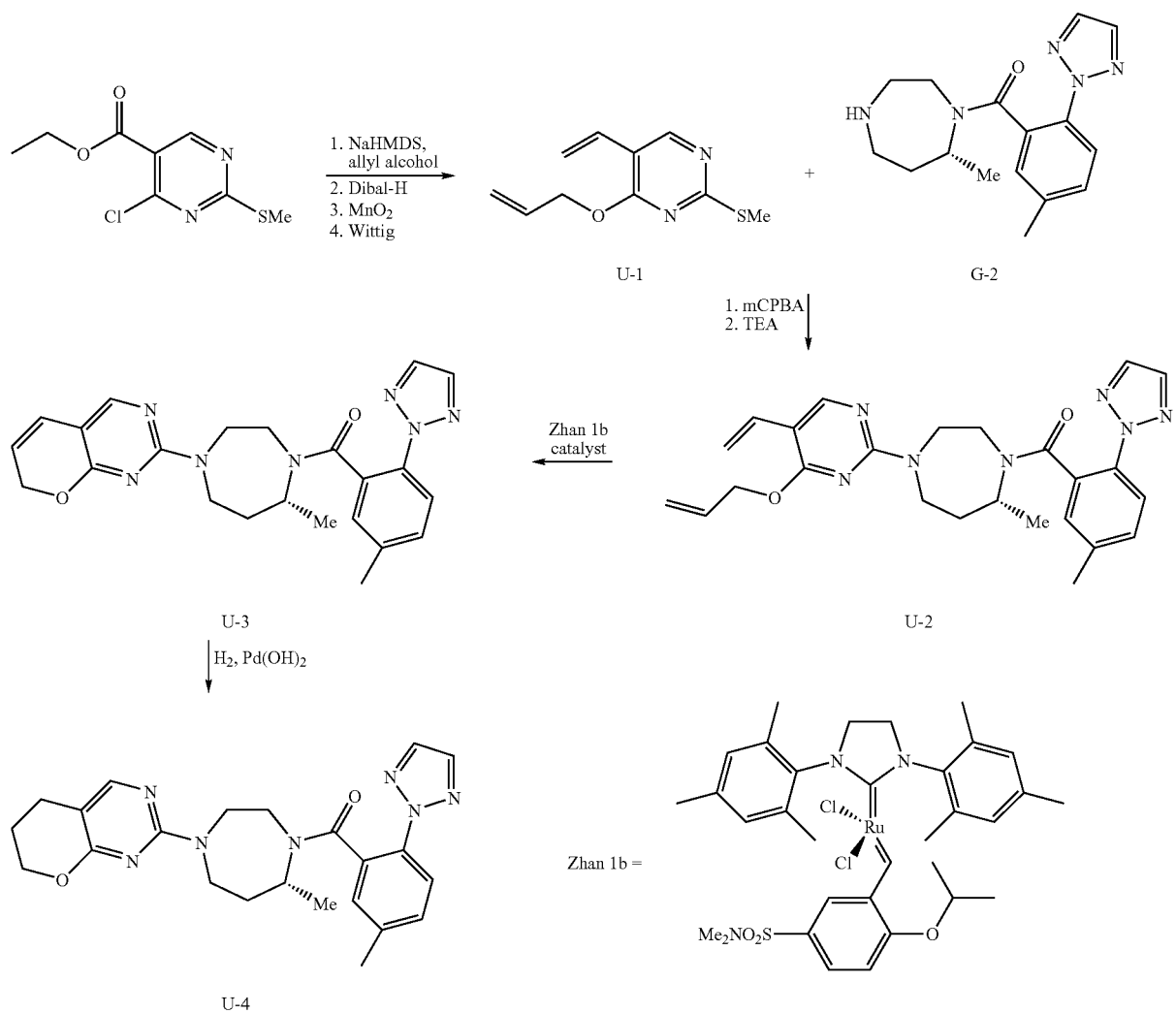

4-(allyloxy)-2-(methylthio)-5-vinylpyrimidine (U-1)

To 3.0 g (12.9 mmol) of ethyl 4-chloro-2-(methylthio) pyrimidine-5-carboxylate in THF (65 mL) was added 1.12 g (19.3 mmol) of allyl alcohol and 6.45 mL (12.9 mmol, 2M in THF) NaHMDS. The reaction was stirred at ambient temperature for 2 h and quenched with brine. The aqueous phase was extracted with EtOAc (4×20 mL), dried over MgSO₄ and concentrated. The crude reaction mixture was re-dissolved in THF (50 mL) and 38.7 mL (38.7 mmol, 1M in THF) of diisobutylaluminum hydride was added at ambient temperature. The reaction was quenched after 45 minutes with saturated sodium-potassium tartrate. The aqueous phase was extracted with EtOAc (4×50 mL), dried over MgSO₄ and concentrated. The residue was purified by flash column chromatography (EtOAc/hexanes) to afford an oil. The resulting oil was dissolved in chloroform (31 mL) and to this solution was added 4.1 g (4.7 mmol) of MnO₂. the reaction was stirred at ambient temperature 4 h, filtered through celite and concentrated to afford a clear oil. The resulting oil was added in THF (10 mL) to a suspension of 8.3 mL (16.7 mmol, 2M in THF) NaHMDS and 6.8 g (19.0 mmol) methyltriphenylphosphonium bromide in THF (40 mL) and the reaction was stirred 2 h. The reaction mixture was quenched with water (50 mL) and extracted with EtOAc (4×50 mL). The combined organic phase was dried over MgSO₄ and concentrated. The residue was purified by flash column chromatography (EtOAc/hexanes) to afford an oil. Data for U-1: LC/MS: rt=2.87 min; m/z (M+H)=208.9 found; 209.1 required.

(5R)-1-[4-(allyloxy)-5-vinylpyrimidin-2-yl]-5-methyl-4-[5-methyl-2-(2H-1,2,3-triazol-2-yl)benzoyl]-1,4-diazepane (U-2)

To 500 mg (2.40 mmol) of U-1 in CH₂Cl₂ (12.0 mL) was added 1.08 g (4.8 mmol) of mCPBA and the mixture was stirred at ambient temperature for 1 hour. The reaction concentrated directly and the residue was dissolved in DMF (10 mL). To the reaction mixture was added 1.67 mL (12.0 mmol) of triethylamine and 1.44 g (4.8 mmol) of G2 and the reaction was heated to 100° C. After 4 h, the reaction was cooled and partitioned between EtOAc and water. The combined organics were dried over MgSO₄ and concentrated. The residue was purified by flash column chromatography (EtOAc/hexanes) to afford U-2 as a foamy solid. Data for U-2: LC/MS: rt=2.30 min; m/z (M+H)=460.3 found; 460.2 required.

2-{(5R)-5-methyl-4-[5-methyl-2-(2H-1,2,3-triazol-2-yl)benzoyl]-1,4-diazepan-1-yl}-7H-pyrano[2,3-d]pyrimidine (U-3)

To 500 mg (1.09 mmol) of U-2 in degassed 1,2-dichloroethane (5.4 mL) was added 0.12 g (4.8 mmol) of Zhan 1 b catalyst and the mixture was stirred at ambient temperature for 15 hours. The reaction was partitioned between EtOAc and water, and the combined organics were dried over MgSO₄ and concentrated. The residue was purified by flash column chromatography (EtOAc/hexanes) to afford U-3 as a foamy solid. Data for U-3: LC/MS: rt=1.69 min; m/z (M+H)=432.2 found; 432.2 required; HRMS m/z (M+H)=432.2155 found; 432.2143 required.

2-{(5R)-5-methyl-4-[5-methyl-2-(2H-1,2,3-triazol-2-yl)benzoyl]-1,4-diazepan-1-yl}-6,7-dihydro-5H-pyrano[2,3-d]pyrimidine (U-4)

To 420 mg (0.97 mmol) of U-3 in degassed ethyl acetate (9.7 mL) was added 68 mg of 20 weight percent palladium hydroxide and the reaction mixture was placed under an atmosphere of hydrogen at ambient temperature. After 2 hours, the reaction was filtered through celite and concentrated. The residue was purified by flash column chromatography (EtOAc/hexanes) to afford U-4 as a foamy solid. Data for U-4: LC/MS: rt=1.63 min; m/z (M+H)=434.2 found; 434.1 required; HRMS m/z (M+H)=434.2312 found; 434.2299 required.

SCHEME V

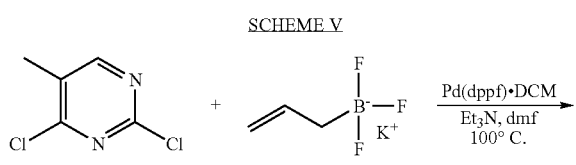

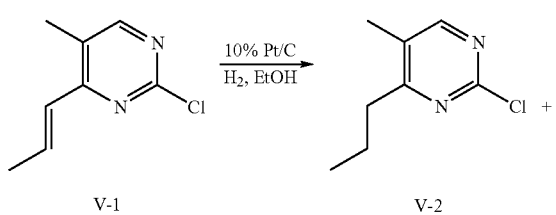

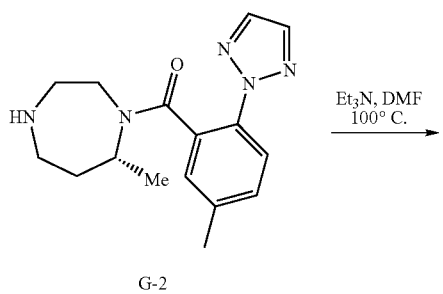

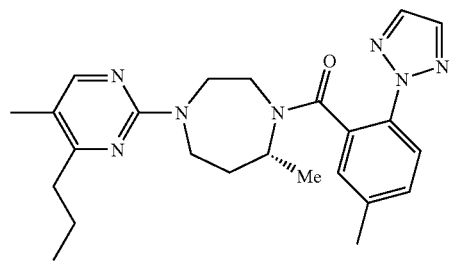

V-3

2-chloro-5-methyl-4-[(1E)-prop-1-en-1-yl]pyrimidine (V-1)

To 1.5 g (9.2 mmol) of 2,4-dichloro-5-methylpyrimidine in DMF (35 mL) was added 1.5 g (10.1 mmol) of potassium allyltrifluoroborate, 150 mg (0.18 mmol) of PdCl₂(dppf)·DCM and 1.54 mL (11 mmol) triethylamine. The reaction was stirred at 100° C. for 15 hours. The reaction was diluted with EtOAc (60 mL), washed with water, saturated sodium bicarbonate solution and brine and concentrated. The residue was purified by flash column chromatography (EtOAc/hexanes) to afford an oil. Data for V-1: LC/MS: rt=2.06 min; m/z (M+H)=169.1 found; 169.6 required.

2le;2q-chloro-5-methyl-4-propylpyrimidine (V-2)

To 550 mg (3.26 mmol) of V-1 in ethanol (10 mL) was added 100 mg of 10% platinum on carbon and the mixture was stirred at ambient temperature under balloon pressure hydrogen gas for 15 hours. The reaction was filtered through celite and concentrated to afford an oil. Data for V-2: LC/MS: rt=2.04 min; m/z (M+H)=171.1 found; 171.6 required.

(5R)-5-methyl-1-(5-methyl-4-propylpyrimidin-2-yl)-4-[5-methyl-2-(2H-1,2,3-triazol-2-yl)benzoyl]-1,4-diazepane (V-3)

A mixture of 289 mg (0.97 mmol) of G-2, 165 mg (0.97 mmol) of V-2 and 674 uL (4.83 mmol) triethylamine in DMF (5 mL) was stirred at 100° C. for 15 hours. The reaction was diluted with EtOAc (60 mL), washed with water, saturated sodium bicarbonate solution and brine and concentrated. The residue was purified by flash column chromatography (EtOAc/hexanes) to afford a foamy solid. Data for V-3: LC/MS: rt=2.30 min; m/z (M+H)=434.2 found; 434.5 required; HRMS m/z (M+H)=434.2667 found; 434.2663 required.

SCHEME W

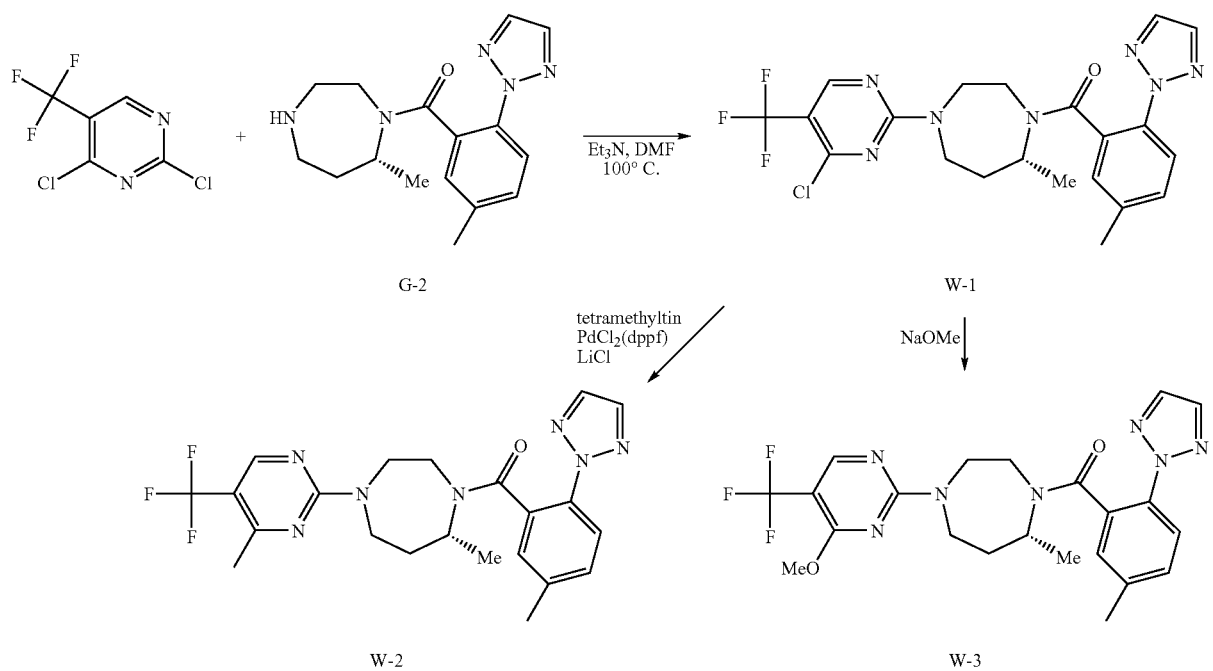

(5R)-1-[4-chloro-5-(trifluoromethyl)pyrimidin-2-yl]-5-methyl-4-[5-methy 1-2-(2H-1,2,3-triazol-2-yl)benzoyl]-1,4-diazepane (W-1)

A mixture of 100 mg (0.33 mmol) of G-2, 87 mg (0.4 mmol) of 2,4-dichloro-5-(trifluoromethyl)pyrimidine and 233 µL (1.67 mmol) triethylamine in DMF (2 mL) was stirred at 100° C. in a microwave synthesizer for 30 minutes. The reaction was diluted with EtOAc (60 mL), washed with water, saturated sodium bicarbonate solution and brine and concentrated. The residue was purified by flash column chromatography (EtOAc/hexanes) to afford a foamy solid. Data for W-1: LC/MS: rt=2.63 min; m/z (M+H)=480.1 found; 480.9 required

(5R)-5-methyl-4-[5-methyl-2-(2H-1,2,3-triazol-2-yl)benzoyl]-1-[4-methyl-5-(trifluoromethyl)pyrimidin-2-yl]1,4-diazepane (W-2)

A mixture of 30 mg (0.063 mmol) of W-1, 22 mg (0.125 mmol) tetramethyltin, 5 mg (0.006 mmol) PdCl$_2$(dppf) and 26 mg (0.625 mmol) LiCl in DMF (1.5 mL) was stirred at 130° C. for 30 minutes. An additional 22 mg (0.125 mmol) of tetramethyltin was added and the reaction stirred for 1 hour more. The reaction was diluted with EtOAc (60 mL), washed with saturated sodium bicarbonate solution and brine and concentrated. The residue was purified by flash column chromatography (EtOAc/hexanes) to afford a foamy solid. Data for W-2: LC/MS: rt=3.48 min; m/z (M+H)=460.0 found; 460.5 required; HRMS m/z (M+H)=460.2090 found; 460.2067 required.

(5R)-1-[4-methoxy-5-(trifluoromethyl)pyrimidin-2-yl]-5-methyl-4-[5-methyl-2-(2H-1,2,3-triazol-2-yl)benzoyl]-1,4-diazepane (W-3)

A mixture of 312 mg (0.65 mmol) of W-1 and 446 µL (1.95 mmol, 4.37 N in methanol) sodium was stirred at room temperature for 30 minutes. The reaction was diluted with EtOAc (60 mL), washed with water, saturated sodium bicarbonate solution and brine and concentrated. The residue was purified by flash column chromatography (EtOAc/hexanes) to afford a foamy solid. Data for W-3: LC/MS: rt=3.27 min; m/z (M+H)=476.0 found; 476.5 required; HRMS m/z (M+H)= 476.2022 found; 476.2017 required.

SCHEME X

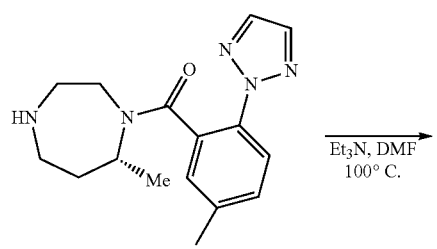

53
-continued

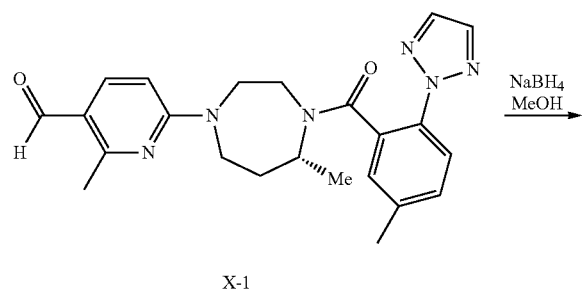

X-1

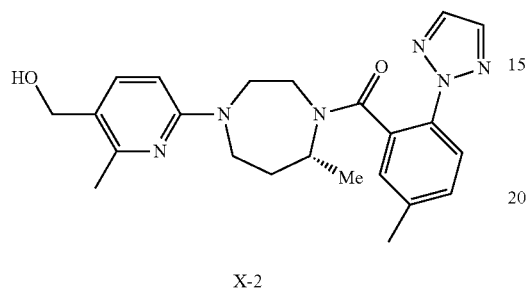

X-2

2-methyl-6-{(5R)-5-methyl-4-[5-methyl-2-(2H-1,2,3-triazol-2-yl)benzoyl]-1,4-diazepan-1-yl}nicotinaldehyde (X-1)

A mixture of 50 mg (0.17 mmol) of G-2, 34 mg (0.22 mmol) of 2,6-dichloropyridine-3-carboxaldehyde and 116 uL (0.84 mmol) triethylamine in DMF (3 mL) was stirred at 100° C. for 45 minutes. The reaction was diluted with EtOAc (60 mL), washed with water, saturated sodium bicarbonate solution and brine and concentrated. The residue was purified by flash column chromatography (EtOAc/hexanes) to afford a foamy solid. Data for W-1: LC/MS: rt=1.96 min; m/z (M+H)=419.1 found; 419.5 required

2-methyl-6-{(5R)-5-methyl-4-[5-methyl-2-(2H-1,2,3-triazol-2-yl)benzoyl]-1,4-diazepan-1-yl}pyridin-3-yl)methanol (X-2)

A mixture of 30 mg (0.072 mmol) of X-1 and 2.7 mg (0.072 mmol) sodium borohydride in methanol (1 mL) was stirred at ambient temperature for 10 minutes. The reaction was diluted with EtOAc (60 mL), washed with water, saturated sodium bicarbonate solution and brine, dried with sodium sulfate and concentrated to afford a solid. Data for X-2: LC/MS: rt=1.25 min; m/z (M+H)=421.2 found; 421.5 required; HRMS m/z (M+H)=421.2347 found; 421.2347 required.

TABLE 1

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cmp | Structure | Name | HRMS m/z (M + H) |
|---|---|---|---|
| 1-1 | 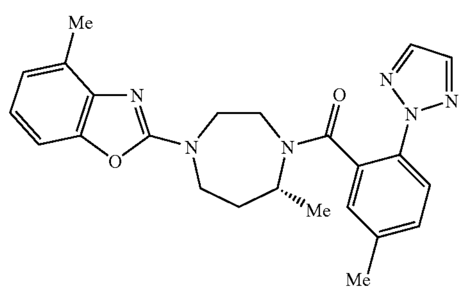 | 4-methyl-2-{(5R)-5-methyl-4-[5-methyl-2-(2H-1,2,3-triazol-2-yl)benzoyl]-1,4-diazepan-1-yl}-1,3-benzoxazole | 431.2202 found, 431.2190 required. |
| 1-2 | 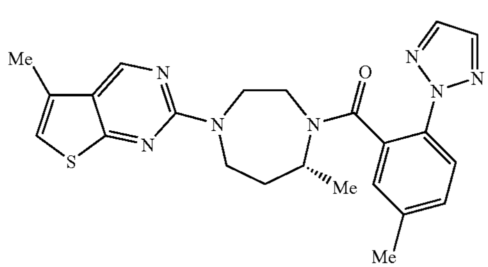 | 5-methyl-2-{(5R)-5-methyl-4-[5-methyl-2-(2H-1,2,3-triazol-2-yl)benzoyl]-1,4-diazepan-1-yl}thieno[2,3-d]pyrimidine | 448.1920 found, 448.1914 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cmp | Structure | Name | HRMS m/z (M + H) |
|---|---|---|---|
| 1-3 | 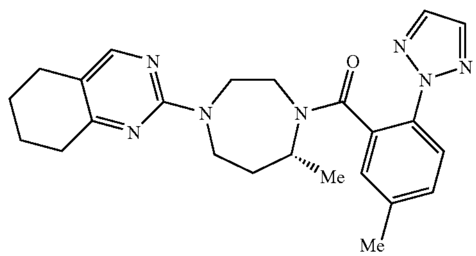 | 2-{(5R)-5-methyl-4-[5-methyl-2-(2H-1,2,3-triazol-2-yl)benzoyl]-1,4-diazepan-1-yl}-5,6,7,8-tetrahydroquinazoline | 432.2515 found, 432.2512 required. |
| 1-4 | 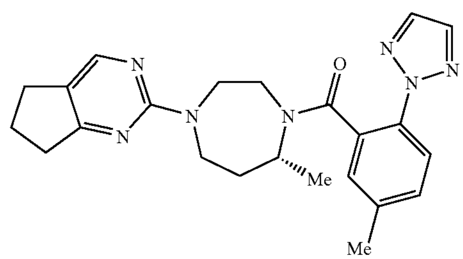 | 2-{(5R)-5-methyl-4-[5-methyl-2-(2H-1,2,3-triazol-2-yl)benzoyl]-1,4-diazepan-1-yl}-6,7-dihydro-5H-cyclopenta[d]pyrimidine | 418.2354 found, 418.2350 required. |
| 1-5 | 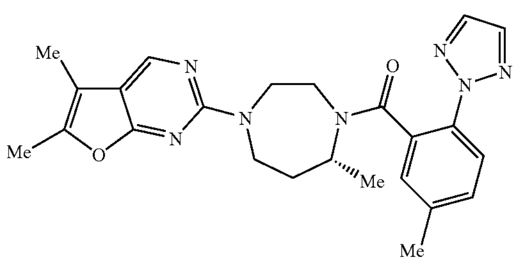 | 5,6-dimethyl-2-{(5R)-5-methyl-4-[5-methyl-2-(2H-1,2,3-triazol-2-yl)benzoyl]-1,4-diazepan-1-yl}furo[2,3-d]pyrimidine | 446.2299 found, 446.2299 required. |
| 1-6 | 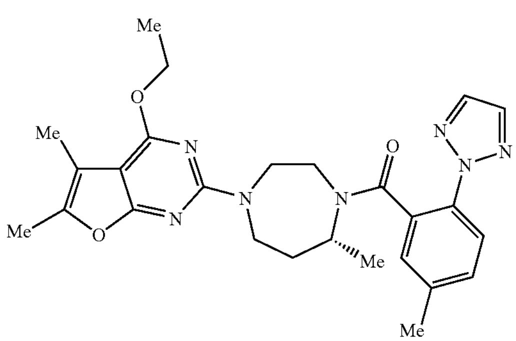 | 4-ethoxy-5,6-dimethyl-2-{(5R)-5-methyl-4-[5-methyl-2-(2H-1,2,3-triazol-2-yl)benzoyl]-1,4-diazepan-1-yl}furo[2,3-d]pyrimidine | 490.2559 found, 490.2561 required. |
| 1-7 | 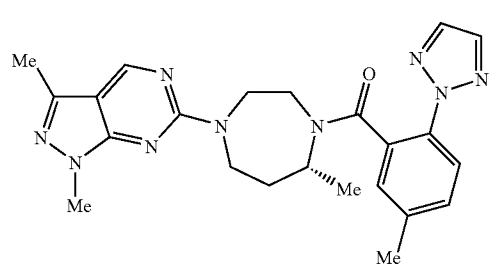 | 1,3-dimethyl-6-{(5R)-5-methyl-4-[5-methyl-2-(2H-1,2,3-triazol-2-yl)benzoyl]-1,4-diazepan-1-yl)-1H-pyrazolo[3,4-d]pyrimidine | 446.2410 found, 446.2412 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cmp | Structure | Name | HRMS m/z (M + H) |
|---|---|---|---|
| 1-8 | 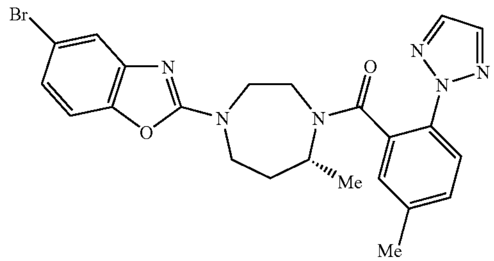 | 5-bromo-2-{(5R)-5-methyl-4-[5-methyl-2-(2H-1,2,3-triazol-2-yl)benzoyl]-1,4-diazepan-1-yl}-1,3-benzoxazole | 495.1164 found, 495.1144 required. |
| 1-9 | 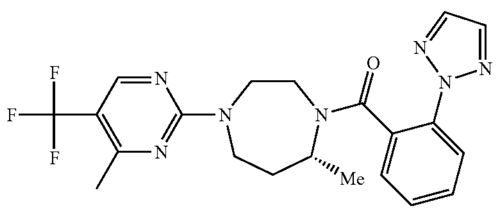 | (5R)-5-methyl-1-[4-methyl-5-(trifluoromethyl)-pyrimidin-2-yl]-4-[2-(2H-1,2,3-triazol-2-yl)benzoyl]-1,4-diazepane | 446.1908 found, 446.1911 required. |
| 1-10 | 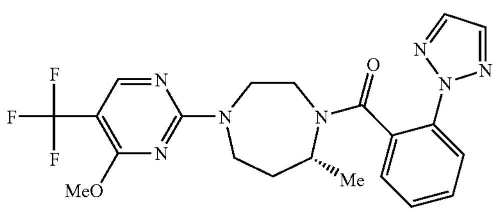 | (5R)-1-[4-methoxy-5-(trifluoromethyl)pyrimidin-2-yl]-5-methyl-4-[2-(2H-1,2,3-triazol-2-yl)benzoyl]-1,4-diazepane | 460.1856 found, 460.1860 required. |

The following compounds are prepared using the foregoing methodology, but substituting the appropriately substituted reagent, as described in the foregoing Reaction Schemes and Examples. The requisite starting materials are commercially available, described in the literature or readily synthesized by one skilled in the art of organic synthesis without undue experimentation: 6-fluoro-2-{(5S)-5-methyl-4-[2-(2H-1,2,3-triazol-2-yl)benzoyl]-1,4-diazepan-1-yl}quinazoline; 5-chloro-2-{(5S)-5-methyl-4-[5-methyl-2-(2H-1,2,3-triazol-2-yl)benzoyl]-1,4-diazepan-1-yl}-1,3-benzoxazole; methyl 3-{[(7S)-4-(5-chloro-1,3-benzoxazol-2-yl)-7-methyl-1,4-diazepan-1-yl]carbonyl}-4-(2H-1,2,3-triazol-2-yl)benzoate; 3-{[(7S)-4-(5-chloro-1,3-benzoxazol-2-yl)-7-methyl-1,4-diazepan-1-yl]carbonyl}-4-(2H-1,2,3-triazol-2-yl)benzoic acid; [3-{[(7S)-4-(5-chloro-1,3-benzoxazol-2-yl)-7-methyl-1,4-diazepan-1-yl]carbonyl}-4-(2H-1,2,3-triazol-2-yl)phenyl]methanol; 6,7-difluoro-2-{(5S)-5-methyl-4-[2-(2H-1,2,3-triazol-2-yl)benzoyl]-1,4-diazepan-1-yl}quinoxaline; 5-methyl-2-{(5S)-5-methyl-4-[2-(2H-1,2,3-triazol-2-yl)benzoyl]-1,4-diazepan-1-yl}thieno[2,3-d]pyrimidine; 2-{(5S)-5-methyl-4-[2-(2H-1,2,3-triazol-2-yl)benzoyl]-1,4-diazepan-1-yl}-5,6,7,8-tetrahydroquinazoline; 2-{(5S)-5-methyl-4-[2-(2H-1,2,3-triazol-2-yl)benzoyl]-1,4-diazepan-1-yl}-6,7-dihydro-5H-cyclopenta[d]pyrimidine; 2-{(5S)-5-methyl-4-[5-methyl-2-(2H-1,2,3-triazol-2-yl)benzoyl]-1,4-diazepan-1-yl}-7,8-dihydroquinolin-5(6H)-one; 6-chloro-2-{(5S)-5-methyl-4-[5-methyl-2-(2H-1,2,3-triazol-2-yl)benzoyl]-1,4-diazepan-1-yl}pyrido[2,3-d]pyrimidin-7(8H)-one; 5-methyl-2-(4-[2-(2H-1,2,3-triazol-2-yl)benzoyl]-1,4-diazepan-1-yl}thieno[2,3]pyrimidin-4-amine; 5-methyl-2-{(5S)-5-methyl-2-(2H-1,2,3-triazol-2-yl)benzoyl]-1,4-diazepan-1-yl}-furo[2,3]pyrimidine; 2-{(5S)-5-methyl-4-[5-methyl-2-(2H-1,2,3-triazol-2-yl)benzoyl]-1,4-diazepan-1-yl}-6,7-dihydro-5H-pyrano[2,3-d]pyrimidine; (5S)-5-methyl-1-(5-methyl-4-propylpyrimidin-2-yl)-4-[5-methyl-2-(2H-1,2,3-triazol-2-yl)benzoyl]-1,4-diazepane; (5S)-1-[4-chloro-5-(trifluoromethyl)pyrimidin-2-yl]-5-methyl-4-[5-methyl-2-(2H-1,2,3-triazol-2-yl)benzoyl]-1,4-diazepane; (5S)-5-methyl-4-[5-methyl-2-(2H-1,2,3-triazol-2-yl)benzoyl]-1-[4-methyl-5-(trifluoromethyl)pyrimidin-2-yl]-1,4-diazepane; (5S)-1-[4-methoxy-5-(trifluoromethyl)pyrimidin-2-yl]-5-methyl-4-[5-methyl-2-(2H-1,2,3-triazol-2-yl)benzoyl]-1,4-diazepane; 2-methyl-6-{(5R)-5-methyl-4-[5-methyl-2-(2H-1,2,3-triazol-2-yl)benzoyl]-1,4-diazepan-1-yl}pyridin-3-yl)methanol; 4-methyl-2-{(5S)-5-methyl-4-[5-methyl-2-(2H-1,2,3-triazol-2-yl)benzoyl]-1,4-diazepan-1-yl}-1,3-benzoxazole; 5-methyl-2-{(5S)-5-methyl-4-[5-methyl-2-(2H-1,2,3-triazol-2-yl)benzoyl]-1,4-diazepan-1-yl}thieno[2,3-d]pyrimidine; 2-{(5S)-5-methyl-4-[5-methyl-2-(2H-1,2,3-triazol-2-yl)benzoyl]-1,4-diazepan-1-yl}-5,6,7,8-tetrahydroquinazoline; 2-{(5S)-5-methyl-4-[5-methyl-2-(2H-1,2,3-triazol-2-yl)benzoyl]-1,4-diazepan-1-yl}-6,7-dihydro-5H-cyclopenta[d]pyrimidine; 5,6-dimethyl-2-{(5S)-5-methyl-4-[5-methyl-2-(2H-1,2,3-triazol-2-yl)benzoyl]-1,4-diazepan-1-yl}furo[2,3-d]pyrimidine; 4-ethoxy-5,6-dimethyl-2-{(5S)-5-methyl-4-[5-methyl-2-(2H-1,2,3-triazol-2-yl)benzoyl]-1,4-diazepan-1-yl}furo[2,3-d]pyrimidine;

1,3-dimethyl-6-{(5S)-5-methyl-4-[5-methyl-2-(2H-1,2,3-triazol-2-yl)benzoyl]-1,4-diazepan-1-yl}-1H-pyrazolo[3,4-d]pyrimidine; 5-bromo-2-{(5S)-5-methyl-4-[5-methyl-2-(2H-1,2,3-triazol-2-yl)benzoyl]-1,4-diazepan-1-yl}-1,3-benzoxazole; (5S)-5-methyl-1-[4-methyl-5-(trifluoromethyl)-pyrimidin-2-yl]-4-[2-(2H-1,2,3-triazol-2-yl)benzoyl]-1,4-diazepane; (5S)-1-[4-methoxy-5-(trifluoromethyl)pyrimidin-2-yl]-5-methyl-4-[2-(2H-1,2,3-triazol-2-yl)benzoyl]-1,4-diazepane.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound which is: 5-chloro-2-{(5R)-5-methyl-4-[5-methyl-2-(2H-1,2,3-triazol-2-yl)benzoyl]-1,4-diazepan-1-yl}-1,3-benzoxazole; or a pharmaceutically acceptable salt thereof.

2. A compound which is 5-chloro-2-{(5R)-5-methyl-4-[5-methyl-2-(2H-1,2,3-triazol-2-yl)benzoyl]-1,4-diazepan-1-yl}-1,3-benzoxazole.

3. A pharmaceutical composition which comprises a pharmaceutically acceptable carrier and a compound which is: 5-chloro-2-{(5R)-5-methyl-4-[5-methyl-2-(2H-1,2,3-triazol-2-yl)benzoyl]-1,4-diazepan-1-yl}-1,3-benzoxazole; or a pharmaceutically acceptable salt thereof.

4. A pharmaceutical composition which comprises a pharmaceutically acceptable carrier and the compound 5-chloro-2-{(5R)-5-methyl-4-[5-methyl-2-(2H-1,2,3-triazol-2-yl)benzoyl]-1,4-diazepan-1-yl}-1,3-benzoxazole.

5. A method for treating insomnia in a human patient in need thereof which comprises administering to the patient a therapeutically effective amount of a compound which is: 5-chloro-2-{(5R)-5-methyl-4-[5-methyl-2-(2H-1,2,3-triazol-2-yl)benzoyl]-1,4-diazepan-1-yl}-1,3-benzoxazole; or a pharmaceutically acceptable salt thereof.

6. A method for treating insomnia in a human patient in need thereof which comprises administering to the patient a therapeutically effective amount of the compound 5-chloro-2-{(5R)-5-methyl-4-[5-methyl-2-(2H-1,2,3-triazol-2-yl)benzoyl]-1,4-diazepan-1-yl}-1,3-benzoxazole.

7. A compound which is 5-chloro-2-{(5R)-5-methyl-4-[5-methyl-2-(2H-1,2,3-triazol-2-yl)benzoyl]-1,4-diazepan-1-yl}-1,3-benzoxazole in the form of a pharmaceutically acceptable salt thereof.

8. A pharmaceutical composition which comprises a pharmaceutically acceptable carrier and the compound 5-chloro-2-{(5R)-5-methyl-4-[5-methyl-2-(2H-1,2,3-triazol-2-yl)benzoyl]-1,4-diazepan-1-yl}-1,3-benzoxazole in the form of a pharmaceutically acceptable salt thereof.

9. A method for treating insomnia in a human patient in need thereof which comprises administering to the patient a therapeutically effective amount of the compound 5-chloro-2-{(5R)-5-methyl-4-[methyl-2-(2H-1,2,3-triazol-2-yl)benzoyl]-1,4-diazepan-1-yl}-1,3-benzoxazole in the form of a pharmaceutically acceptable salt thereof.

* * * * *